(12) United States Patent
Abe et al.

(10) Patent No.: US 12,324,793 B2
(45) Date of Patent: Jun. 10, 2025

(54) METHOD FOR RENAL PROTECTION

(71) Applicants: TOHOKU UNIVERSITY, Sendai (JP); NIPPON CHEMIPHAR CO., LTD., Tokyo (JP)

(72) Inventors: Michiaki Abe, Sendai (JP); Seizo Koshiba, Sendai (JP); Koichiro Nishioka, Tokyo (JP); Kazuhiko Kawaguchi, Tokyo (JP); Satomi Yamasaki, Tokyo (JP); Yasuyuki Teranaka, Tokyo (JP)

(73) Assignees: TOHOKU UNIVERSITY, Sendai (JP); NIPPON CHEMIPHAR CO., LTD., Tokyo (JP)

( * ) Notice: Subject to any disclaimer, the term of this patent is extended or adjusted under 35 U.S.C. 154(b) by 1028 days.

(21) Appl. No.: 17/284,862

(22) PCT Filed: Oct. 17, 2019

(86) PCT No.: PCT/JP2019/040995
§ 371 (c)(1),
(2) Date: Apr. 13, 2021

(87) PCT Pub. No.: WO2020/080499
PCT Pub. Date: Apr. 23, 2020

(65) Prior Publication Data
US 2021/0386696 A1   Dec. 16, 2021

(30) Foreign Application Priority Data

Oct. 17, 2018  (JP) .................... 2018-195568
Oct. 17, 2018  (JP) .................... 2018-195810
Feb. 25, 2019  (JP) .................... 2019-032126
Apr. 28, 2019  (JP) .................... 2019-086945
Jun. 27, 2019  (JP) .................... 2019-119297

(51) Int. Cl.
*A61K 31/194*   (2006.01)
*A61P 13/02*    (2006.01)
*A61P 13/12*    (2006.01)

(52) U.S. Cl.
CPC ........... *A61K 31/194* (2013.01); *A61P 13/02* (2018.01); *A61P 13/12* (2018.01)

(58) Field of Classification Search
CPC .................................................. A61P 13/02
See application file for complete search history.

(56) References Cited

U.S. PATENT DOCUMENTS

| | | | |
|---|---|---|---|
| 2013/0302305 A1* | 11/2013 | Saha | A61K 31/426 424/94.4 |
| 2018/0000764 A1* | 1/2018 | Hernández Miramontes | A61K 9/0014 |
| 2021/0121426 A1 | 4/2021 | Abe et al. | |
| 2023/0293467 A1 | 9/2023 | Abe et al. | |

FOREIGN PATENT DOCUMENTS

| | | | | |
|---|---|---|---|---|
| EP | 3 219 315 A1 | 9/2017 | | |
| EP | 3 616 721 A1 | 3/2020 | | |
| JP | H11180864 A | * | 7/1999 | |
| JP | 2006-193428 A | 7/2006 | | |
| JP | 2009-525276 A | 7/2009 | | |
| JP | 2018-177752 A2 | 11/2018 | | |
| TW | 200940075 A | * | 10/2009 | .......... A61K 31/194 |
| UA | 86173 U | * | 12/2013 | |
| WO | 2007/089571 A2 | 8/2007 | | |
| WO | 2009032538 A1 | 3/2009 | | |
| WO | WO-2017120311 A1 | * | 7/2017 | .......... A61K 31/194 |
| WO | 2018/193648 A1 | 10/2018 | | |
| WO | 2018/193752 A1 | 10/2018 | | |

OTHER PUBLICATIONS

Phisitkul, S. et al. "Amelioration of metabolic acidosis in patients with low GFR reduced kidney endothelin production and kidney injury, and better preserved GFR", Kidney Int'l, vol. 77, Iss 7, Apr. 2010, p. 617-623. (Year: 2010).*

Kopple, J. et al., "Risks of chronic metabolic acidosis in patients with chronic kidney disease", Kidney Int'l, vol. 67, Supplement 95 (2005), pp S21-S27. (Year: 2005).*

Allen, L. et al. (ed), Ansel's Pharm. Dosage Forms and Drug Delivery Systems, 2005 8th ed., LIppincott Williams & Wilkins, p. 51.*

Takatera Koji et al., "Effects of Citric Acid and Lemon Juice on Iron Absorption and Improvement of Anemia in Iron-Deficient Rats", Food Science and Technology Research, vol. 18, No. 1,2012, pp. 127-130, XP093051272.

Huanmei Zhang et al., "Improved iron bioavailability in an oat-based beverage: the combined effect of citric acid addition, dephytinization and iron supplementation", European Journal of Nutrition, vol. 46, No. 2. 2007, pp. 95-102, XP019491022.

O'Neil-Cutting Mary A., "The Effect of Antacids on the Absorption of Simultaneously Ingested Iron", JAMA: The Journal of the American Medical Association, vol. 255, No. 11, Mar. 21, 1986, pp. 1468-1470, XP093051274.

Farahani Heydar, et al., "Study on the Effect of Sodium Bicarbonate in Serum Iron TIBC on Rats", Journal of Arak University of Medical Sciences, 2000, vol. 3, Issue 2, pp. 1-3, XP093051275, http://jams.arakmu.ac.ir/browse.php?a_id=6621&sid=1&slc_lang=en.

Extended European Search Report dated Jun. 13, 2023 in Application No. 20799485.6.

(Continued)

*Primary Examiner* — Gina C Justice

(74) *Attorney, Agent, or Firm* — Sughrue Mion, PLLC

(57) ABSTRACT

The present invention relates to a pharmaceutical composition for renal protection in chronic kidney disease, which contains a citric acid, a pharmaceutically acceptable salt of a citric acid, or a hydrate thereof; and a mixture of the citric acid, the pharmaceutically acceptable salt of the citric acid, and the hydrate thereof, and is a tablet.

8 Claims, 3 Drawing Sheets

(56) References Cited

OTHER PUBLICATIONS

Japanese Office Action dated Jan. 23, 2024 in Japanese Application No. 2020-553318.
Japanese Office Action dated Jan. 23, 2024 in Japanese Application No. 2021-517161.
Toblli, et al., "Potassium citrate administration ameliorates tubulointerstitial lesions in rats with uric acid nephropathy", Clinical Nephrology, 2001, vol. 55, No. 1, pp. 59-68 (12 pages total).
Hostutler, et al., "Transient proximal renal tubular acidosis and Fanconi syndrome in a dog", Journal of the American Veterinary Medical Association, 2004, vol. 224, No. 10, pp. 1611-1614 (4 pages total).
Okamoto, et al., "Growth hormone therapy for a patient with idiopathic Fanconi syndrome and growth hormone deficiency", CEN case reports, 2017, vol. 6, No. 1, pp. 85-87 (3 pages total).
Afzal, et al., "Renal Tubular Acidosis Type 1 with Nephrocalcinosis, Osteomalacia Sub Nephrotic Proteinuria and Subclinical Sjogren's Syndrome—A Case Report", Pakistan Journal of Medical and Health Sciences, 2016, vol. 10, No. 4, pp. 1445-1447 (3 pages total).
Tubular acidosis, [online], Oct. 1, 2014, Childhood Chronic Specific Disease Information Center, <URL: https://www.shouman.jp/disease/details/02_12_032/>, pp. 1-5 (5 pages total).
Fanconi's syndrome, [online], Oct. 1, 2014, Childhood Chronic Specific Disease Information Center, <URL: https://www.shouman.jp/disease/details/02_20_050/>, pp. 1-4 (4 pages total).
Fishbane, et al., "Effects of Ferric Citrate in Patients with Nondialysis-Dependent CKD and Iron Deficiency Anemia", Journal of American Society of Nephrology, 2017, vol. 28, pp. 1851-1858 (8 pages total).
Sorot Phisitkul et al: "Amelioration of metabolic acidosis in patients with low GFR reduced kidney endothelin production and kidney injury, and better preserved GFR", Kidney International, 2010, vol. 77, No. 7, pp. 617-623 (8 pages total).
Pipeleers L et al: "Pre-terminal renal insufficiency in a patient with enteric hyperoxaluria: effect of medical management on renal function", Acta Clinica Belgica: Sociétés Cliniques Des Hôpitaux De Belgique; Société Belge De Biologie Clinique / Société Belge De Médecine Interne, Belgium, 2012, vol. 67, No. 1, pp. 39-41 (4 pages total).
Ou Yan et al: "Citrate Attenuates Adenine-Induced Chronic Renal Failure in Rats by Modulating the Th17/Treg Cell Balance", Inflammation, Plenum Press, New York, NY, US, 2015, vol. 39, No. 1, pp. 79-86 (8 pages total).
Tanner George A. et al: "Citrate therapy for polycystic kidney disease in rats", Kidney International, 2000, vol. 58, No. 5, pp. 1859-1869 (12 pages total).
Kim Sejoong et al: "Effects of Sodium Citrate on Salt Sensitivity and Kidney Injury in Chronic Renal Failure", Journal of Korean Medical Sciences, 2014, vol. 29, No. 12, pp. 1658-1664 (8 pages total).
Domrongkitchaiporn Somnuek et al: "Dosage of potassium citrate in the correction of urinary abnormalities in pediatric distal renal tubular acidosis patients", American Journal of Kidney Diseases, 2002, vol. 39, No. 2, pp. 383-391 (10 pages total).
Extended European Search Report dated Sep. 29, 2022 in European Application No. 19873714.0.
Igor Loniewski, et al. "Bicarbonate therapy for prevention of chronic kidney disease progression", Kidney International, 2014, vol. 85, pp. 529-535 (7 pages).
Uralyt Package insert of Uralyt Tablet, amended in Mar. 2014, 8th edition, Uralyt, Nippon Chemiphar Co., Ltd. (4 pages).
United States Office Action dated Oct. 1, 2024 in U.S. Appl. No. 17/606,125.
"Pink Grapefruit Flavoured Hydration Tabs", HNC Healthy Nutrition Company, Maxi Nutrition, Mintel, Sep. 2018, (4 pages) <https://www.gnpd.com/sinatra/recordpage/5961515/>.
"CKD Treatment Guide", Japanese Society of Nephrology, 2012, pp. 1-4 (5 pages).
Hamada Toshihiro., Prog. Med., 2005, vol. 25, pp. 1726-1731 (6 pages).
"CP-107", Program and Abstracts of the Annual Meeting of the Japanese Society of Hypertension, 2004, p. 170 (2 pages).
"Chemiphamation Plus", 2017, No. 3 (2 pages total) [https://www.nc-medical.com/deteil/chemiphamation01_03.pdf].
Australian Office Action dated Jul. 9, 2024 in Application No. 2019361520.
Japanese Office Action dated Aug. 20, 2024 in Application No. 2020-553318.
Ione De Brito-Ashurst et al., "Bicarbonate Supplementation Slows Progression of CKD and Improves Nutritional Status", J. Am. Soc. Nephrol, 2009, pp. 2075-2084, vol. 20.
Tomokazu Souma et al., "Luminal Alkalinization Attenuates Proteinuria-Induced Oxidative Damage in Proximal Tubular Cells", J. Am. Soc. Nephrol, 2011, pp. 635-648, vol. 22.
Tatsuo Yamamoto et al., "Urinary Angiotensinogen as a Marker of Intrarenal Angiotensin II Activity Associated with Deterioration of Renal Function in Patients with Chronic Kidney Disease", J. Am. Soc. Nephrol, 2007, pp. 1558-1565, vol. 18.
Liliana Gadola et al., "Calcium citrate ameliorates the progression of chronic renal injury", Kidney International, Apr. 2004, pp. 1224-1230, vol. 65.
Wanghui Jing et al., "Phosphate Binder, Ferric Citrate, Attenuates Anemia, Renal Dysfunction, Oxidative Stress, Inflammation, and Fibrosis in 5/6 Nephrectomized CKD Rats", The Journal of Pharmacology and Experimental Therapeutics, Oct. 2018, pp. 129-137, vol. 367.
Krissanapong Manotham et al., "Citrate Attenuates Tubulointerstitial, Fibrosis in 5/6 Nephrectomized Rats by Decreasing Transforming Growth Factor-", Journal of the Medical Association of Thailand, Sep. 2006, pp. S168-S177, vol. 89.
Satoko Tsuchida , "Oral drugs used in the treatment of acidemia and their use", Lectures in Pediatrics, Apr. 2001, pp. 170-173, vol. 1, No. 1.
Michiaki Abe et al., "Examination of uremic substances purified by medicinal blood purification by oral alkalinizing agents", subject publication of the 60th Annual Meeting of the Japanese Society of Nephrology, Mar. 2017 (1 page).
International Search Report of PCT/JP2019/040995 dated Jan. 21, 2020 [PCT/ISA/210].
International Search Report of PCT/JP2020/017690 dated Jun. 23, 2020 [PCT/ISA/210].
Communication dated Apr. 30, 2024 issued by the Japanese Patent Office in application No. 2021-517161.

\* cited by examiner eGFR vs Urine pH (Spot-Morning): Citrate (6–24w)

eGFR vs Urine pH (Spot-Morning): Bicarbonate (6–24w)

METHOD FOR RENAL PROTECTION

CROSS REFERENCE TO RELATED APPLICATIONS

This application is a National Stage of International Application No. PCT/JP2019/040995, filed Oct. 17, 2019, claiming priority to Japanese Patent Application No. 2018-195568, filed Oct. 17, 2018, Japanese Patent Application No. 2018-195810, filed Oct. 17, 2018, Japanese Patent Application No. 2019-032126, filed Feb. 25, 2019, Japanese Patent Application No. 2019-086945, filed Apr. 28, 2019, and Japanese Patent Application No. 2019-119297, filed Jun. 27, 2019, the contents of all of which are incorporated herein by reference in their entirety.

TECHNICAL FIELD

The present invention relates to a pharmaceutical composition for renal protection and a pharmaceutical composition for renal function diagnosis, each of which contain a citric acid, a pharmaceutically acceptable salt of a citric acid, or a hydrate thereof, or a mixture of the citric acid, the pharmaceutically acceptable salt of citric acid, and the hydrate thereof.

Further, the present invention relates to a pharmaceutical composition for suppression of intrarenal renin-angiotensin system activation and further for suppression of acidosis or improvement of aciduria in a patient with chronic kidney disease, which contains a citric acid, a pharmaceutically acceptable salt of a citric acid, or a hydrate thereof; or a mixture of the citric acid, the pharmaceutically acceptable salt of citric acid, and the hydrate thereof.

BACKGROUND ART

The number of patients with end-stage kidney disease (ESKD) requiring dialysis or transplantation is increasing worldwide. The number of dialysis patients is increasing also in Japan, and is 320,000 at the end of 2014.

As a preliminary disease of the ESKD, chronic kidney disease (CKD) is recognized. The CKD is a concept including a kidney disease that continues chronically regardless of the primary disease, and is a concept including all the pathological conditions in which there is a decrease in renal function expressed by a glomerular filtration rate (GFR) or findings suggesting kidney disorder are observed persistently and chronically (three months or more). Since the CKD is not only a risk of progression to ESKD but also a strong risk of developing cardiovascular disease (CVD), it is extremely important to detect the CKD in the early stage and conduct an appropriate treatment. A large number of CKD treatment methods have been established so far, but such methods are still insufficient, and development of a renal protective agent has been demanded.

In a patient with advanced CKD, since the concentration of bicarbonate ions ($HCO_3^-$) in blood lowers and metabolic acidosis develops, an alkaline agent such as sodium bicarbonate, or a citric acid preparation is administered. Further, it has been reported that the progress of CKD is suppressed by the administration of sodium bicarbonate that is an alkaline agent (Non Patent Literature 1). In addition, it has been reported that in an animal model with nephrotic syndrome caused by protein overload, the tubular cell damage due to aciduria is suppressed by oral administration of sodium bicarbonate (Non Patent Literature 2). Further, it is known that by the administration of an alkaline agent to a patient with early-stage CKD, the progress of kidney injury is suppressed and the concentration of uremic substances in blood is decreased (Patent Literatures 1 and 2).

However, it is not known that renal function can be evaluated by using an alkalizing agent such as a citric acid preparation.

In addition, in recent years, numerous kidney injury markers for CKD and acute kidney injury (AKI) have been reported.

It is known that the activation of a renin-angiotensin system (may be sometimes abbreviated as RAS) in the kidney is deeply involved in the progress of not only hypertension but also kidney injury. Angiotensinogen in the kidney is involved in the development and progress mechanism of hypertension and kidney injury. Further, it has been reported that the angiotensinogen excreted in urine shows a positive correlation with the angiotensinogen expressed in the kidney (Non Patent Literature 3).

8-hydroxy-2'-deoxyguanosine (8-OHdG) is one of the oxidative stress markers that have been most widely used at present, and it is known that the 8-OHdG production is increased by kidney injury.

However, it is not known that by the administration of an alkaline agent to a patient with CKD or AKI, the angiotensinogen concentration in urine and the oxidative stress can be suppressed.

CITATION LIST

Patent Literature

Patent Literature 1: WO 2018/193648 A
Patent Literature 2: WO 2018/193752 A

Non Patent Literature

Non Patent Literature 1: Brito-Ashurst, I. D., et al., Bicarbonate supplementation slows progression of CKD and improves nutritional status. J. Am. Soc. Nephrol., 20: 2075-2084, 2009.
Non Patent Literature 2: Souma T., et al., Luminal alkalinization attenuates proteinuria-induced oxidative damage in proximal tubular cells. J. Am. Soc. Nephrol., 22: 635-648, 2011.
Non Patent Literature 3: J. Am. Soc. Nephrol, 18: pp. 1558-1565, 2007

SUMMARY OF INVENTION

Technical Problem

An object of the present invention is to provide a pharmaceutical composition for renal protection, containing a citric acid, a pharmaceutically acceptable salt of a citric acid, or a hydrate thereof; or a mixture of the citric acid, the pharmaceutically acceptable salt of citric acid, and the hydrate thereof. Another object of the present invention is to provide a pharmaceutical composition for renal function diagnosis, containing a citric acid, a pharmaceutically acceptable salt of a citric acid, or a hydrate thereof; or a mixture of the citric acid, the pharmaceutically acceptable salt of citric acid, and the hydrate thereof. Another object of the present invention is to provide a medicine useful for suppression of intrarenal RAS activation and treatment or prevention of acidosis in a patient with chronic kidney disease, or for suppression of intrarenal RAS activation and improvement of aciduria in a patient with chronic kidney disease. Another object of the present invention is to provide a medicine useful for suppression of oxidative stress in the kidney. Another object of the present invention is to provide a food for renal protection or for suppression of oxidative stress.

Solution to Problem

As a result of intensive studies to achieve the objects described above, the present inventors have found that a composition containing a citric acid, a pharmaceutically acceptable salt of a citric acid, or a hydrate thereof; or a mixture of the citric acid, the pharmaceutically acceptable salt of citric acid, and the hydrate thereof is useful for renal protection and evaluation of renal function, and thus have completed the present invention.

Further, the present inventors have found that a composition containing a citric acid, a pharmaceutically acceptable salt of a citric acid, or a hydrate thereof; or a mixture of the citric acid, the pharmaceutically acceptable salt of citric acid, and the hydrate thereof is useful for suppression of the increase in angiotensinogen concentration in urine as compared to sodium bicarbonate, or for suppression of the 8-OHdG concentration in urine, and have also found that the medicament is useful for suppression of intrarenal RAS activation and at the same time suppression of acidosis in a patient with chronic kidney disease, for suppression of intrarenal RAS activation and at the same time improvement of aciduria in a patient with chronic kidney disease, or for suppression of oxidative stress in the kidney, and thus have completed the present invention.

One aspect of the present invention is to provide a pharmaceutical composition for renal protection in chronic kidney disease, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a pharmaceutical composition for renal function diagnosis, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a method for determining a renal function, including administering to a subject a pharmaceutical composition that contains a citric acid, a pharmaceutically acceptable salt of a citric acid, or a hydrate thereof; or a mixture of the citric acid, the pharmaceutically acceptable salt of citric acid, and the hydrate thereof, and measuring a pH of spot urine of the subject after the administration.

One aspect of the present invention is to provide a method for determining a renal function, including administering to a subject a pharmaceutical composition that contains a citric acid, a pharmaceutically acceptable salt of a citric acid, or a hydrate thereof; or a mixture of the citric acid, the pharmaceutically acceptable salt of citric acid, and the hydrate thereof, and measuring a pH of early-morning urine of the subject before the administration and a pH of spot urine of the subject after the administration.

One embodiment of the present invention is to provide a pharmaceutical composition for suppression of acidosis or improvement of aciduria in a patient with chronic kidney disease with hypertension, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a pharmaceutical composition for suppression of oxidative stress in the kidney, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a pharmaceutical composition for suppression of increase in 8-OHdG concentration in urine, for suppression of increase in $\beta_2$-microglobulin concentration in urine, for suppression of the increase in albumin concentration in urine, or for suppression of increase in protein concentration in spot urine, with the progress of chronic kidney disease, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a pharmaceutical composition useful for maintenance or improvement of renal tubular function in chronic kidney disease, or for suppression of decrease in renal tubular function in chronic kidney disease, which contains a citric acid, a pharmaceutically acceptable salt of a citric acid, or a hydrate thereof; or a mixture of the citric acid, the pharmaceutically acceptable salt of citric acid, and the hydrate thereof.

One aspect of the present invention is to provide a food for renal protection or for suppression of oxidative stress in the kidney, which contains a citric acid, a pharmaceutically acceptable salt of a citric acid, or a hydrate thereof; or a mixture of the citric acid, the pharmaceutically acceptable salt of citric acid, and the hydrate thereof.

Advantageous Effects of Invention

By a pharmaceutical composition or a food composition, provided by the present invention, the kidney in chronic kidney disease is protected. By a pharmaceutical composition provided by the present invention, renal function can be evaluated.

By a pharmaceutical composition, a food composition, or the like, which is provided by the present invention, intrarenal renin-angiotensin system activation can be suppressed and at the same time acidosis can be suppressed in a patient with chronic kidney disease, and intrarenal renin-angiotensin system activation can be suppressed and at the same time aciduria can be improved in a patient with chronic kidney disease.

DESCRIPTION OF EMBODIMENTS

1. Pharmaceutical Composition

Figure 1:
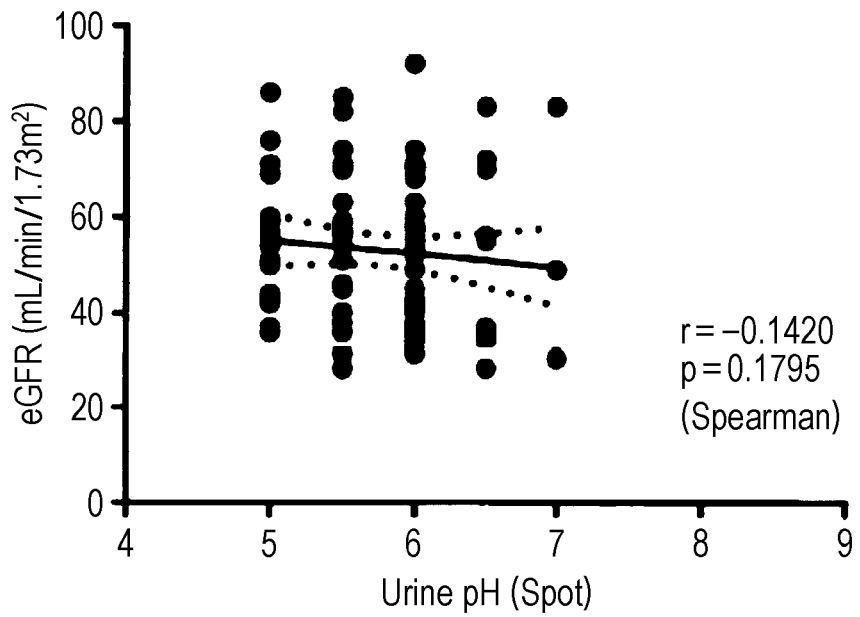
FIG. 1 is a diagram showing a correlation between the pH of spot urine and the eGFR in a control group.

A pharmaceutical composition provided by the present invention may contain citric acid, a pharmaceutically acceptable salt of a citric acid, a pharmaceutically acceptable salt of a citric acid, or a hydrate thereof; or a mixture of the citric acid, the pharmaceutically acceptable salt of citric acid, and the hydrate thereof, as an active component.

An example of the pharmaceutically acceptable salt of citric acid includes an alkali metal salt of citric acid. Examples of the alkali metal salt of citric acid include potassium citrate, and sodium citrate, and may include a stable hydrate such as a monohydrate of potassium citrate ($C_6H_5K_3O_7 \cdot H_2O$) and a dihydrate of sodium citrate ($C_6H_5Na_3O_7 \cdot 2H_2O$).

Preferred examples of the active component, which is contained in the pharmaceutical composition provided by the present invention, include sodium citrate, potassium citrate, a hydrate of the sodium citrate or the potassium citrate, or a mixture of the sodium citrate, the potassium citrate, or the hydrate, and may include, for example, a mixture of a monohydrate of potassium citrate ($C_6H_5K_3O_7 \cdot H_2O$) and a dihydrate of sodium citrate ($C_6H_5Na_3O_7 \cdot 2H_2O$). A mixture ratio of the monohydrate of potassium citrate ($C_6H_5K_3O_7 \cdot H_2O$) to the dihydrate of sodium citrate ($C_6H_5Na_3O_7 \cdot 2H_2O$) may be appropriately set by a person skilled in the art, and for example, as to the molar ratio of the monohydrate of potassium citrate to the dihydrate of sodium citrate, the dihydrate of sodium citrate may be set to 0.01 to 100 with respect to 1 of the monohydrate of potassium citrate. The molar ratio of potassium citrate (for example, monohydrate of potassium citrate) to sodium citrate (for example, dihydrate of sodium citrate) may be appropriately set by a person skilled in the art, and may be set to, for example, 0.85:1.15 to 1.15:0.85, 0.90:1.10 to 1.10:0.90, 0.95:1.05 to 1.05:0.95, or 0.99:1.01 to 1.01:0.99, and is preferably 1:1.

Further, another example of the active component, which is contained in the pharmaceutical composition provided by the present invention, includes sodium citrate or a hydrate thereof, and may include, for example, a dihydrate of sodium citrate ($C_6H_5Na_3O_7 \cdot 2H_2O$).

In addition, another example of the active component, which is contained in the pharmaceutical composition provided by the present invention, includes potassium citrate or a hydrate thereof, and may include, for example, a monohydrate of potassium citrate ($C_6H_5K_3O_7 \cdot H_2O$).

In one embodiment, the active component, which is contained in the pharmaceutical composition of the present invention, may include a mixture of sodium citrate or a hydrate thereof and potassium citrate or a hydrate thereof.

In one embodiment, the active component, which is contained in the pharmaceutical composition of the present invention, may be a mixture of potassium citrate, sodium citrate, and citric acid (for example, anhydrous citric acid). In that case, the mixture ratio of the citric acid (for example, anhydrous citric acid), the potassium citrate, and the sodium citrate may be appropriately set by a person skilled in the art, and may be set to, for example, 1:1.7 to 2.3:1.7 to 2.3, 1:1.9 to 2.1:1.9 to 2.1, or 1:1.95 to 2.05:1.95 to 2.05, and is preferably 1:2:2.

In one embodiment, the active component, which is contained in the pharmaceutical composition of the present invention, may be a mixture of a monohydrate of potassium citrate ($C_6H_5K_3O_7 \cdot H_2O$), a dihydrate of sodium citrate ($C_6H_5Na_3O_7 \cdot 2H_2O$), and anhydrous citric acid. In that case, a mixture ratio of the anhydrous citric acid, the monohydrate of potassium citrate ($C_6H_5K_3O_7 \cdot H_2O$), and dihydrate of sodium citrate ($C_6H_5Na_3O_7 \cdot 2H_2O$) may be appropriately set by a person skilled in the art, and may be set to, for example, 1:1.7 to 2.3:1.7 to 2.3, 1:1.9 to 2.1:1.9 to 2.1, or 1:1.95 to 2.05:1.95 to 2.05, and is preferably 1:2:2.

In one embodiment, the active component, which is contained in the pharmaceutical composition of the present invention, may be formed of only a mixture of sodium citrate or a hydrate thereof and potassium citrate or a hydrate thereof.

In the present specification, when referring to a weight of a citric acid, a pharmaceutically acceptable salt of a citric acid, or a hydrate thereof; or a mixture of the citric acid, the pharmaceutically acceptable salt of citric acid, and the hydrate thereof (for example, monohydrate of potassium citrate ($C_6H_5K_3O_7 \cdot H_2O$) and dihydrate of sodium citrate ($C_6H_5Na_3O_7 \cdot 2H_2O$)), the weight can be on a dry basis.

The pharmaceutical composition provided by the present invention can be used for diagnosis of renal function. The pharmaceutical composition for renal function diagnosis provided by the present invention may contain as the active component, a citric acid, a pharmaceutically acceptable salt of a citric acid, or a hydrate thereof; or a mixture of the citric acid, the pharmaceutically acceptable salt of citric acid, and the hydrate thereof, (for example, mixture of sodium citrate or a hydrate thereof and potassium citrate or a hydrate thereof, such as a mixture of a monohydrate of potassium citrate ($C_6H_5K_3O_7 \cdot H_2O$) and a dihydrate of sodium citrate ($C_6H_5Na_3O_7 \cdot 2H_2O$)).

Accordingly, in one embodiment, the present invention is to provide a pharmaceutical composition for renal function diagnosis, containing a citric acid, a pharmaceutically acceptable salt of a citric acid, or a hydrate thereof; or a mixture of the citric acid, the pharmaceutically acceptable salt of citric acid, and the hydrate thereof.

Further, in one embodiment, the present invention provides a method for determining a renal function of a subject, including administering to the subject a pharmaceutical composition for renal function diagnosis, which contains a citric acid, a pharmaceutically acceptable salt of a citric acid, or a hydrate thereof; or a mixture of the citric acid, the pharmaceutically acceptable salt of citric acid, and the hydrate thereof, and measuring a pH of urine of the subject after the administration.

The mixing amount of the active component in the pharmaceutical composition for renal function diagnosis provided by the present invention is not particularly limited, and for example, in a case where the pharmaceutical composition for renal function diagnosis is a tablet, 231.5 mg of potassium citrate ($C_6H_5K_3O_7 \cdot H_2O$) and 195.0 mg of sodium citrate hydrate ($C_6H_5Na_3O_7 \cdot 2H_2O$) may be contained in one tablet.

The pharmaceutical composition for renal function diagnosis provided by the present invention can be used for diagnosis of glomerular filtration function, and can be an indicator for improvement or deterioration of eGFR, or an indicator of eGFR itself.

The pharmaceutical composition for renal function diagnosis provided by the present invention may be administered to a subject in need of evaluation of the renal function, and for example, may be administered to a patient with chronic kidney disease, or a patient with acute kidney disease.

In one embodiment, a kit that includes the pharmaceutical composition for renal function diagnosis provided by the present invention, together with an instrument for measuring the pH of urine, a reagent (for example, pH test paper), and the like is provided.

The pharmaceutical composition for renal function diagnosis provided by the present invention is administered to a subject (for example, human) in need of evaluation of the renal function, and the renal function can be evaluated by measuring the pH of urine of the subject after the administration. The administration may be performed at anytime in the morning, daytime, or evening, and as the frequency of the administration, it is not particularly limited, and a single administration is preferable. After the administration, the timing of measuring the pH of urine can also be appropriately set, and may be set to a time after the lapse of, for example, 1 hour, 2 hours, 3 hours, 4 hours, 5 hours, or 6 hours from the administration. The pH of urine can be measured by a measurement method known in the technical field to which the invention belongs, and may be measured by, for example, a pH test paper. Preferably, by measuring the pH of the first urine after administration of the pharmaceutical composition for renal function diagnosis provided by the present invention, the renal function of the administered subject can be determined.

In one embodiment, the pharmaceutical composition for renal function diagnosis provided by the present invention can also be used for determination of renal function of a patient who has been subjected to treatment or prevention of chronic kidney disease or acute kidney disease (for example, patient to which a medicine for treatment or prevention of chronic kidney disease or acute kidney disease, such as a urine alkalizing agent has been administered) or determination of the effect of the above-described treatment or prevention. For example, before the above-described treatment or prevention (for example, administration of a medicine for treatment or prevention), the pharmaceutical composition for renal function diagnosis provided by the present invention is administered, and the pH of urine (for example, spot urine collected for the first time after administration) is measured after the administration (this measured pH value is taken as a value A), and after the above-described treatment or prevention (for example, administration of a medicine for treatment or prevention), the pharmaceutical composition for renal function diagnosis provided by the present invention is administered, and the pH of urine (for example, spot urine collected for the first time after administration) is measured after the administration (this measured pH value is taken as a value B), and if the value B is higher than the value A, it can be determined that the renal function has been improved by the above-described treatment or prevention (for example, administration of a medicine for treatment or prevention). Conversely, for example, before the above-described treatment or prevention (for example, administration of a medicine for treatment or prevention), the pharmaceutical composition for renal function diagnosis provided by the present invention is administered, and the pH of urine (for example, spot urine collected for the first time after administration) is measured after the administration (this measured pH value is taken as a value A), and after the above-described treatment or prevention (for example, administration of a medicine for treatment or prevention), the pharmaceutical composition for renal function diagnosis provided by the present invention is administered, and the pH of urine (for example, spot urine collected for the first time after administration) is measured after the administration (this measured pH value is taken as a value B), and if the value B is lower than the value A, it can be determined that the renal function has been deteriorated by the above-described treatment or prevention (for example, administration of a medicine for treatment or prevention). In this embodiment, a medicine for the above-described treatment or prevention (for example, urine alkalizing agent) may be administered continuously, (for example, for 6 weeks, 12 weeks, 24 weeks, 48 weeks, or 72 weeks), and the pharmaceutical composition for renal function diagnosis provided by the present invention is administered before and after the continuous administration, the pH of urine (for example, spot urine collected for the first time after administration) is measured after the administration, and the improvement or deterioration of the renal function may be determined. Further, in this embodiment, in a case where the administered medicine for treatment or prevention of chronic kidney disease or acute kidney disease and the pharmaceutical composition for renal function diagnosis provided by the present invention are the same medicament, the medicament administered immediately before the pH measurement of urine can be the pharmaceutical composition for renal function diagnosis provided by the present invention.

In one embodiment, irrespective of the administration of the pharmaceutical composition for renal function diagnosis provided by the present invention, the renal function can be evaluated by measuring the pH of early-morning urine of a subject (for example, human) in need of evaluation of the renal function. In this embodiment, a subject of which the renal function is to be evaluated may be a patient who has been subjected to treatment or prevention of chronic kidney disease or acute kidney disease (for example, patient to which a medicine for treatment or prevention of chronic kidney disease or acute kidney disease, such as a urine alkalizing agent has been administered). The medicine for treatment or prevention of chronic kidney disease or acute kidney disease (for example, urine alkalizing agent) may be administered in a single dose or continuously, but the early-morning urine to be subjected to pH measurement can be an early-morning urine on the day before and/or the day after the administration of the medicine for treatment or prevention of chronic kidney disease or acute kidney disease (for example, urine alkalizing agent).

In one embodiment, in order to determine the renal function of a patient who has been subjected to treatment or prevention of chronic kidney disease or acute kidney disease (for example, patient to which a medicine for treatment or prevention of chronic kidney disease or acute kidney disease, such as a urine alkalizing agent has been administered) or to determine the effect of the above-described treatment or prevention, the pH of early-morning urine (for example, early-morning urine collected for the last time before the above-described treatment or prevention) before the above-described treatment or prevention (for example, administration of a medicine for treatment or prevention) is measured (this measured pH value is taken as a value A), and the pH of early-morning urine (for example, early-morning urine collected for the first time after the above-described treatment or prevention) after the above-described treatment or prevention (for example, administration of a medicine for treatment or prevention) is measured (this measured pH value is taken as a value B), and if the value B is higher than the value A, it can be determined that the renal function has been improved by the above-described treatment or prevention (for example, administration of a medicine for treatment or prevention). Conversely, for example, before the above-described treatment or prevention (for example, administration of a medicine for treatment or prevention), the pH of early-morning urine (for example, early-morning urine collected for the last time before the above-described treatment or prevention) is measured (this measured pH value is taken as a value A), and after the above-described treatment or prevention (for example, administration of a medicine for treatment or prevention), the pH of early-morning urine (for example, early-morning urine collected for the first time after the above-described treatment or prevention) is measured (this measured pH value is taken as a value B), and if the value B is lower than the value A, it can be determined that the renal function has been deteriorated by the above-described treatment or prevention (for example, administration of a medicine for treatment or prevention). In this embodiment, a medicine for the above-described treatment or prevention (for example, urine alkalizing agent) may be administered continuously, (for example, for 6 weeks, 12 weeks, 24 weeks, 48 weeks, or 72 weeks), and the pH of early-morning urine may be measured before and after the continuous administration to determine the improvement or deterioration of the renal function.

Further, in one embodiment, the pharmaceutical composition for renal function diagnosis provided by the present invention is administered to a subject (for example, human) in need of evaluation of the renal function, and by measuring the pH of early-morning urine (for example, early-morning urine collected for the last time before administration) of the subject before the administration and the pH of urine (for example, spot urine collected for the first time after administration) of the subject after the administration, the renal function can be evaluation. The administration may be performed at anytime in the morning, daytime, or evening, but preferably in the morning, and as the frequency of the administration, it is not particularly limited, and a single administration is preferable. After the administration of the pharmaceutical composition for renal function diagnosis provided by the present invention, the timing of measuring the pH of urine can be appropriately set, and may be set to a time after the lapse of, for example, 1 hour, 2 hours, 3 hours, 4 hours, 5 hours, or 6 hours from the administration, and the pH of urine (spot urine) collected for the first time after the administration of the pharmaceutical composition for renal function diagnosis provided by the present invention may be measured. The early-morning urine can be an early-morning urine collected for the last time before the administration of the pharmaceutical composition for renal function diagnosis provided by the present invention. For example, the early-morning urine may be an early-morning urine collected by 1 hour, 2 hours, 3 hours, 4 hours, 5 hours, or 6 hours before the administration of the pharmaceutical composition for renal function diagnosis provided by the present invention. Further, for example, the urine (spot urine) collected for the first time after the administration of the pharmaceutical composition for renal function diagnosis provided by the present invention and the early-morning urine collected for the last time before the administration of the pharmaceutical composition for renal function diagnosis provided by the present invention, which are subjected to pH measurement, can be urines collected on the same day.

In one embodiment, when the difference between the pH value (this pH value is taken as a value A) of urine (for example, spot urine collected for the first time after administration) of a subject after the administration of the pharmaceutical composition for renal function diagnosis provided by the present invention and the pH value (this pH value is taken as a value B) of early-morning urine (for example, early-morning urine collected for the last time before administration) of the subject before the administration (the value A−the value B) is −1 or less, the eGFR value of the subject can be determined to be less than 50.

In addition, in one embodiment, when the difference between the pH value (this pH value is taken as a value A) of urine (for example, spot urine collected for the first time after administration) of a subject after the administration of the pharmaceutical composition for renal function diagnosis provided by the present invention and the pH value (this pH value is taken as a value B) of early-morning urine (for example, early-morning urine collected for the last time before administration) of the subject before the administration (the value A−the value B) is 1 or more, the eGFR value of the subject can be determined to be 50 or more.

Further, in one embodiment, the pharmaceutical composition for renal function diagnosis provided by the present invention can also be used for determination of the renal function of a patient who has been subjected to treatment or prevention of chronic kidney disease or acute kidney disease (for example, patient to which a medicine for treatment or prevention of chronic kidney disease or acute kidney disease, such as a urine alkalizing agent has been administered) or determination of the effect of the above-described treatment or prevention. For example, before the above-described treatment or prevention (for example, administration of a medicine for treatment or prevention), the pharmaceutical composition for renal function diagnosis provided by the present invention is administered, the difference between the pH value (this pH value is taken as a value A) of urine (for example, spot urine collected for the first time after administration) of a subject after the administration and the pH value (this pH value is taken as a value B) of early-morning urine (for example, early-morning urine collected for the last time before administration) of the subject before the administration (the value A−the value B) is calculated, and after the above-described treatment or prevention (for example, administration of a medicine for treatment or prevention), the pharmaceutical composition for renal function diagnosis provided by the present invention is administered, the difference between the pH value (this pH value is taken as a value C) of urine (for example, spot urine collected for the first time after administration) of the subject after the administration and the pH value (this pH value is taken as a value D) of early-morning urine (for example, early-morning urine collected for the last time before administration) of the subject before the administration (the value C−the value D) is calculated. If (the value C−the value D) is higher than (the value A−the value B), it can be determined that the renal function has been improved by the above-described treatment or prevention (for example, administration of a medicine for treatment or prevention). Conversely, for example, before the above-described treatment or prevention (for example, administration of a medicine for treatment or prevention), the pharmaceutical composition for renal function diagnosis provided by the present invention is administered, the difference between the pH value (this pH value is taken as a value A) of urine (for example, spot urine collected for the first time after administration) of a subject after the administration and the pH value (this pH value is taken as a value B) of early-morning urine (for example, early-morning urine collected for the last time before administration) of the subject before the administration (the value A−the value B) is calculated, and after the above-described treatment or prevention (for example, administration of a medicine for treatment or prevention), the pharmaceutical composition for renal function diagnosis provided by the present invention is administered, the difference between the pH value (this pH value is taken as a value C) of urine (for example, spot urine collected for the first time after administration) of the subject after the administration and the pH value (this pH value is taken as a value D) of early-morning urine (for example, early-morning urine collected for the last time before administration) of the subject before the administration (the value A−the value B) is calculated. If (the value C−the value D) is lower than (the value A−the value B), it can be determined that the renal function has been deteriorated by the above-described treatment or prevention (for example, administration of a medicine for treatment or prevention). In this embodiment, a medicine for the above-described treatment or prevention of (for example, urine alkalizing agent) may be administered continuously, (for example, for 6 weeks, 12 weeks, 24 weeks, 48 weeks, or 72 weeks), and the pharmaceutical composition for renal function diagnosis provided by the present invention is administered before and after the continuous administration, the pH of early-morning urine (for example, early-morning urine collected for the last time before administration) before the administration of the pharmaceutical composition for renal function diagnosis provided by the present invention, and the pH of urine (for example, spot urine collected for the first time after administration) after the administration of the pharmaceutical composition for renal function diagnosis provided by the present invention are measured, and then the improvement or deterioration of the renal function may be determined. In this embodiment, the early-morning urine collected before the administration of the pharmaceutical composition for renal function diagnosis provided by the present invention and the spot urine collected after the administration of the pharmaceutical composition for renal function diagnosis provided by the present invention, which are subjected to pH measurement, can be urines collected on the same day. Further, in this embodiment, in a case where the administered medicine for treatment or prevention of chronic kidney disease or acute kidney disease and the pharmaceutical composition for renal function diagnosis provided by the present invention are the same medicament, the medicament administered immediately before the pH measurement of urine can be the pharmaceutical composition for renal function diagnosis provided by the present invention.

The pharmaceutical composition provided by the present invention can be used also for renal protection in chronic kidney disease. The renal protection includes protection of renal tissues, and protection of renal function.

For example, the pharmaceutical composition provided by the present invention can be a pharmaceutical composition for protection of renal tissues in chronic kidney disease, a pharmaceutical composition for suppression of renal tissue damage with the progress of chronic kidney disease, a pharmaceutical composition for maintenance or improvement of renal function in chronic kidney disease, or a pharmaceutical composition for suppression of decrease in renal function with the progress of chronic kidney disease.

An example of the renal tissues, which are protected with the pharmaceutical composition provided by the present invention, includes renal tubules (for example, proximal renal tubules).

Further, an example of the renal function, which is maintained or improved by the pharmaceutical composition provided by the present invention, includes renal tubular function (for example, proximal renal tubular function), and an example of the renal tubular function includes urinary concentrating capacity.

Accordingly, the pharmaceutical composition provided by the present invention can also be a pharmaceutical composition for maintenance or improvement of renal tubular function in chronic kidney disease, a pharmaceutical composition for suppression of decrease in renal tubular function with the progress of chronic kidney disease, a pharmaceutical composition for maintenance or improvement of urinary concentrating capacity in chronic kidney disease, or a pharmaceutical composition for suppression of decrease in urinary concentrating capacity with the progress of chronic kidney disease.

Such effects of the pharmaceutical composition provided by the present invention can be evaluated by measuring with a method known in the technical field to which the invention belongs the 8-OHdG concentration in early-morning urine, the $\beta_2$-microglobulin concentration in early-morning urine, the albumin concentration in early-morning urine, the albumin concentration in spot urine, the protein concentration in spot urine, and/or the osmotic pressure of early-morning urine, in a patient with chronic kidney disease to which the pharmaceutical composition provided by the present invention has been administered.

For example, in a case where by the administration of the pharmaceutical composition provided by the present invention to a patient with chronic kidney disease, the 8-OHdG concentration in early-morning urine of the patient with chronic kidney disease is lowered as compared with that before the administration, it may be evaluated that the renal function is protected by the pharmaceutical composition provided by the present invention.

For example, in a case where the 8-OHdG concentration in early-morning urine of a patient with chronic kidney disease to which the pharmaceutical composition provided by the present invention has been administered is lower than that of a patient with chronic kidney disease to which the pharmaceutical composition provided by the present invention has not been administered, it may be evaluated that the renal tissue damage with the progress of chronic kidney disease is suppressed by the pharmaceutical composition provided by the present invention.

For example, in a case where by the administration of the pharmaceutical composition provided by the present invention to a patient with chronic kidney disease, the $\beta_2$-microglobulin concentration in early-morning urine of the patient with chronic kidney disease is lowered as compared with that before the administration, it may be evaluated that the renal tubular tissues are protected by the pharmaceutical composition provided by the present invention.

For example, in a case where the $\beta_2$-microglobulin concentration in early-morning urine of a patient with chronic kidney disease to which the pharmaceutical composition provided by the present invention has been administered is lower than that of a patient with chronic kidney disease to which the pharmaceutical composition provided by the present invention has not been administered, it may be evaluated that the renal tubular tissue damage with the progress of chronic kidney disease is suppressed by the pharmaceutical composition provided by the present invention.

For example, in a case where by the administration of the pharmaceutical composition provided by the present invention to a patient with chronic kidney disease, the albumin concentration in early-morning urine, the albumin concentration in spot urine, and/or the protein concentration in spot urine, of the patient with chronic kidney disease are not increased as compared with those before the administration, it may be evaluated that the renal function is maintained or improved by the pharmaceutical composition provided by the present invention.

For example, in a case where the albumin concentration in early-morning urine, the albumin concentration in spot urine, and/or the protein concentration in spot urine, of a patient with chronic kidney disease to which the pharmaceutical composition provided by the present invention has been administered are lower than those of a patient with chronic kidney disease to which the pharmaceutical composition provided by the present invention has not been administered, it may be evaluated that the decrease in renal function with the progress of chronic kidney disease is suppressed by the pharmaceutical composition provided by the present invention.

For example, in a case where by the administration of the pharmaceutical composition provided by the present invention to a patient with chronic kidney disease, the osmotic pressure of early-morning urine of the patient with chronic kidney disease is not lowered as compared with that before the administration, it may be evaluated that the renal tubular function is maintained or improved by the pharmaceutical composition provided by the present invention, and it may be evaluated that the urinary concentrating capacity is maintained or improved by the pharmaceutical composition provided by the present invention.

For example, in a case where the osmotic pressure of early-morning urine of a patient with chronic kidney disease to which the pharmaceutical composition provided by the present invention has been administered is higher than that of a patient with chronic kidney disease to which the pharmaceutical composition provided by the present invention has not been administered, it may be evaluated that the decrease in renal tubular function with the progress of chronic kidney disease is suppressed by the pharmaceutical composition provided by the present invention, and it may be evaluated that the decrease in urinary concentrating capacity with the progress of chronic kidney disease is suppressed by the pharmaceutical composition provided by the present invention.

In one embodiment, since the pharmaceutical composition provided by the present invention decreases the 8-OHdG concentration in urine, which can be an indicator for oxidative stress in the kidney, the pharmaceutical composition can be a pharmaceutical composition for suppression of oxidative stress in the kidney of a patient with chronic kidney disease. The decrease in the 8-OHdG concentration in urine can be evaluated in a comparison between before and after the administration of the pharmaceutical composition provided by the present invention, or in a comparison between administration and non-administration of the pharmaceutical composition provided by the present invention.

Further, in one embodiment, with the administration of the pharmaceutical composition provided by the present invention, the activation of an intrarenal renin-angiotensin system is suppressed, and the acidosis can be treated or prevented and the aciduria can be improved, in a patient with chronic kidney disease, and therefore, the pharmaceutical composition provided by the present invention can be a pharmaceutical composition for treatment or prevention of acidosis in a patient with chronic kidney disease with hypertension, or a pharmaceutical composition for improvement of aciduria in a patient with chronic kidney disease with hypertension.

The "suppression of intrarenal renin-angiotensin system activation" can be evaluated with the suppression of the increase in the angiotensinogen concentration in urine after administration of the pharmaceutical composition provided by the present invention, in comparison with that in the angiotensinogen concentration in urine before the administration, or can be evaluated with the suppression of the increase in the angiotensinogen concentration in urine by administration of the pharmaceutical composition provided by the present invention, in comparison with that in placebo administration or control.

Further, in one embodiment, with the administration of the pharmaceutical composition provided by the present invention, the increase in 8-OHdG concentration in urine (for example, in early-morning urine), the increase in angiotensinogen concentration in urine (for example, in early-morning urine), the increase in $\beta_2$-microglobulin in urine (for example, in early-morning urine), the increase in albumin concentration in urine (for example, in early-morning urine), the increase in albumin concentration in urine (for example, in spot urine), the increase in protein concentration in urine (for example, in spot urine), or the decrease in osmotic pressure of urine (for example, early-morning urine) is suppressed, and therefore, the pharmaceutical composition provided by the present invention can be a pharmaceutical composition for suppression of the increase in 8-OHdG concentration in urine (for example, in early-morning urine), for suppression of the increase in angiotensinogen concentration in urine (for example, in early-morning urine), for suppression of the increase in $\beta_2$-microglobulin in urine (for example, in early-morning urine), for suppression of the increase in albumin concentration in urine (for example, in early-morning urine), for suppression of the increase in albumin concentration in urine (for example, in spot urine), for suppression of the increase in protein concentration in urine (for example, in spot urine), or for suppression of the decrease in osmotic pressure of urine (for example, early-morning urine). These effects can also be evaluated in a comparison between before and after the administration of the pharmaceutical composition provided by the present invention, and in a comparison between the administration group of the pharmaceutical composition provided by the present invention and the placebo or control group.

In the present specification, the term "suppression" is a concept that includes stopping or slowing down the deterioration or progress of a symptom, condition, or disease, and for that purpose, and includes improvement of the symptom, the condition, or the disease, or for that purpose. In this regard, the term "improvement" is a concept that includes making a "pathological" or "abnormal" symptom, condition, or disease closer to the "healthy" or "normal" condition, or for that purpose, and making a "pathological" or "abnormal" symptom, condition, or disease to the "healthy" or "normal" condition, or for that purpose. Accordingly, in one embodiment, the term "improvement" includes that a numerical value, which can be an indicator of the "pathological" or "abnormal" symptom or condition, becomes smaller or larger to come closer to or reach the normal value in accordance with the "improvement". The above expression "deterioration or progress of a symptom, condition, or disease" includes that deterioration or progress of a "pathological" or "abnormal" symptom, condition, or disease, and deterioration or progress of a "pathological" or "abnormal" symptom, condition, or disease from the "healthy" or "normal" condition. In one embodiment, the term "suppression" refers to stopping or slowing down the deterioration or progress of a symptom, condition, or disease, or for that purpose. In another embodiment, the term "suppression" refers to stopping or slowing down the deterioration or progress of a symptom, condition, or disease.

In the present specification, the term "healthy" refers to the absence of acute or chronic disease or disorder, and the term "normal" refers that a healthy subject is in a condition to be normally expressed.

In this regard, the symptom, condition, or disease is compared between before and after the administration of the pharmaceutical composition provided by the present invention, or is compared between when the pharmaceutical composition provided by the present invention is administered and when the control or placebo is administered.

In the present specification, the term "treatment" is a concept that includes eliminating, completely recovering from, curing, or achieving a remission of a "pathological" or "abnormal" symptom, condition, or disease, or for that purpose, includes "suppression" of deterioration of a "pathological" or "abnormal" symptom, condition, or disease and for that purpose, and includes "improvement" of the symptom, condition, or disease. In this regard, the terms "suppression" and "improvement" have the meanings as described above. In one embodiment, the term "treatment" refers to eliminating, completely recovering from, curing, or achieving a remission of a "pathological" or "abnormal" symptom, condition, or disease, or for that purpose. In another embodiment, the term "treatment" refers to eliminating, completely recovering from, curing, or achieving a remission of a "pathological" or "abnormal" symptom, condition, or disease.

In the present specification, the term "prevention" is a concept that includes prevention of development of a "pathological" or "abnormal" symptom, condition, or disease in advance, and for that purpose.

In the present specification, the expression "early-morning urine" refers to a urine collected for the first time after waking up, and the expression "spot urine" refers to any urine other than the "early-morning urine".

The pharmaceutical composition provided by the present invention is administered orally or parenterally to a human or other mammals, and examples of the parenteral administration include intravenous administration, subcutaneous administration, intramuscular administration, intraarticular administration, transmucosal administration, transdermal administration, transnasal administration, rectal administration, intrathecal administration, intraperitoneal administration, and topical administration.

The pharmaceutical composition provided by the present invention may be prepared by using a citric acid, a pharmaceutically acceptable salt of a citric acid, or a hydrate thereof; or a mixture of the citric acid, the pharmaceutically acceptable salt of citric acid, and the hydrate thereof, which is an active component, as it is or by being mixed with a pharmaceutically acceptable carrier, for example, an excipient (such as lactose, D-mannitol, crystalline cellulose, or glucose), a binding agent (such as hydroxypropyl cellulose (HPC), gelatin, or polyvinyl pyrrolidone (PVP)), a lubricating agent (such as magnesium stearate, or talc), a disintegrant (such as starch, or carboxymethyl cellulose calcium (CMC-Ca)), a diluent (such as water for injection, or saline solution), and other additive agents (such as a pH adjusting agent, a surfactant, a solubilizer, a preservative, an emulsifier, an isotonizing agent, and a stabilizer) as needed, and can be a preparation such as a tablet, a capsule, a suspension, an injection, or a suppository. For example, in order to form a tablet, a citric acid, a pharmaceutically acceptable salt of a citric acid, or a hydrate thereof; or a mixture of the citric acid, the pharmaceutically acceptable salt of citric acid, and the hydrate thereof, which is an active component, may be mixed with an excipient (such as lactose, D-mannitol, crystalline cellulose, or glucose), a disintegrant (such as starch, or carboxymethyl cellulose calcium (CMC-Ca)), a binding agent (such as hydroxypropyl cellulose (HPC), gelatin, or polyvinyl pyrrolidone (PVP)), a lubricating agent (such as magnesium stearate, or talc), and formulated into a tablet.

In one embodiment, the pharmaceutical composition provided by the present invention is a tablet. The tablet provided by the present invention may contain a citric acid, a pharmaceutically acceptable salt of a citric acid, or a hydrate thereof; or a mixture of the citric acid, the pharmaceutically acceptable salt of citric acid, and the hydrate thereof, which is an active component, (for example, potassium citrate or a hydrate thereof, sodium citrate or a hydrate thereof, a mixture of a monohydrate of potassium citrate and a dihydrate of sodium citrate, or sodium bicarbonate), and further a pharmaceutically acceptable additive agent that is conventionally used in the field of pharmaceuticals. Examples of the additive agent include an excipient, a binding agent, a disintegrant, a fluidizer, a flavoring agent, a lubricating agent, a pH adjusting agent, a surfactant, a stabilizer, and a flavor.

The content of a citric acid, a pharmaceutically acceptable salt of a citric acid, or a hydrate thereof; or a mixture of the citric acid, the pharmaceutically acceptable salt of citric acid, and the hydrate thereof, which is an active component in the tablet provided by the present invention, may be 10 to 95% by weight, preferably 30 to 90% by weight, and more preferably 60 to 85% by weight with respect to the tablet.

The pharmaceutical composition provided by the present invention can be produced by a method known in the field of pharmaceuticals.

In one embodiment, the hardness of the obtained tablet can be 10 to 200 N, and preferably 30 to 150 N.

The amount of a citric acid, a pharmaceutically acceptable salt of a citric acid, or a hydrate thereof; or a mixture of the citric acid, the pharmaceutically acceptable salt of citric acid, and the hydrate thereof, which is an active component in the pharmaceutical composition provided by the present invention can be appropriately set.

In one embodiment, as to the amount of a citric acid, a pharmaceutically acceptable salt of a citric acid, or a hydrate thereof; or a mixture of the citric acid, the pharmaceutically acceptable salt of citric acid, and the hydrate thereof, which is an active component in the pharmaceutical composition provided by the present invention, the dosage of a citric acid, a pharmaceutically acceptable salt of a citric acid, or a hydrate thereof; or a mixture of the citric acid, the pharmaceutically acceptable salt of citric acid, and the hydrate thereof, which is an active component, may be set to an amount at which aciduria in gout or hyperuricemia is improved by being administered to a human, or less than the amount, and may also be set, for example, so as to be 1 to 50%, or 10 to 20% of the daily dose for improvement of aciduria in gout or hyperuricemia, approved in Japan (for example, two tablets at a time, each containing 231.5 mg of potassium citrate ($C_6H_5K_3O_7 \cdot H_2O$) and 195.0 mg of sodium citrate hydrate ($C_6H_5Na_3O_7 \cdot 2H_2O$) are orally administered 3 times a day, and in a case where the alkaline agent is sodium bicarbonate, 3 to 5 g per day of sodium bicarbonate is orally administered).

In one embodiment, the pharmaceutical composition provided by the present invention is a tablet, and a monohydrate of potassium citrate or a dihydrate of sodium citrate may be contained in an amount of 10 mg to 1 g, preferably 100 mg to 500 mg, and more preferably 400 mg to 500 mg, in one tablet.

In one embodiment, the pharmaceutical composition provided by the present invention is a tablet, and a monohydrate of potassium citrate and a dihydrate of sodium citrate may be contained each in an amount of 10 mg to 300 mg and in a total amount of 20 mg to 600 mg, preferably each in an amount of 150 to 250 mg and in a total amount of 400 to 500 mg, and more preferably each in an amount of 190 to 240 mg and in a total amount of 400 to 450 mg, in one tablet.

In one embodiment, the pharmaceutical composition provided by the present invention is a tablet, and contains 231.5 mg of a monohydrate of potassium citrate and 195.0 mg of a dihydrate of sodium citrate, and may contain as additive agents, anhydrous citric acid, crystalline cellulose, partially pregelatinized starch, hydroxypropyl cellulose, magnesium stearate, hypromellose, macrogol 6000, titanium oxide, and carnauba wax.

As one embodiment, a tablet containing 231.5 mg of a monohydrate of potassium citrate and 195.0 mg of a dihydrate of sodium citrate may be used as one dosage unit.

In the present specification, the expression "dosage unit" refers to a unit of a preparation, and the expression "one dosage unit" refers to the smallest unit of the preparation. Accordingly, for example, in a case of tablets, the dosage unit is each tablet, and one dosage unit refers to one tablet. In a case of injection, the dosage unit is an injection contained in a sealed container such as an ampule, or a vial, and one dosage unit refers to an injection contained in a sealed container such as an ampule, or a vial.

In a case where the pharmaceutical composition provided by the present invention is administered to a human or other mammal, 1 or 2 or more dosage units may be administered at a time, or may be divided to be administered.

The dosage of a citric acid, a pharmaceutically acceptable salt of a citric acid, or a hydrate thereof; or a mixture of the citric acid, the pharmaceutically acceptable salt of citric acid, and the hydrate thereof, which is an active component, is appropriately determined depending on the administration method, and the age, body weight, sex, symptoms, and sensitivity to the medicament of a subject to be administered, and may be adjusted depending on the circumstance of improvement of the symptoms.

In one embodiment, in a case where a mixture of a monohydrate of potassium citrate and a dihydrate of sodium citrate is orally administered to a human, the administration may be performed by using as a daily dose half the daily dose for improvement of aciduria in gout or hyperuricemia, approved in Japan (for example, in a case of a citric acid preparation, two tablets at a time, each containing 231.5 mg of potassium citrate ($C_6H_5K_3O_7 \cdot H_2O$) and 195.0 mg of sodium citrate hydrate ($C_6H_5Na_3O_7 \cdot 2H_2O$) are orally administered 3 times a day).

In one embodiment, in a case where a mixture of a monohydrate of potassium citrate and a dihydrate of sodium citrate is orally administered to a human, the administration may be performed by using as a daily dose the daily dose for improvement of aciduria in gout or hyperuricemia, approved in Japan (for example, in a case of a citric acid preparation, two tablets at a time, each containing 231.5 mg of potassium citrate ($C_6H_5K_3O_7 \cdot H_2O$) and 195.0 mg of sodium citrate hydrate ($C_6H_5Na_3O_7 \cdot 2H_2O$) are orally administered 3 times a day).

In one embodiment, in a case where a mixture of a monohydrate of potassium citrate and a dihydrate of sodium citrate is orally administered to a human, the administration may be started by using as a daily dose half the daily dose for improvement of aciduria in gout or hyperuricemia, approved in Japan (for example, in a case of a citric acid preparation, two tablets at a time, each containing 231.5 mg of potassium citrate ($C_6H_5K_3O_7 \cdot H_2O$) and 195.0 mg of sodium citrate hydrate ($C_6H_5Na_3O_7 \cdot 2H_2O$) are orally administered 3 times a day), and then the dosage may be increased up to the daily dose for improvement of aciduria in gout or hyperuricemia, approved in Japan.

In one embodiment, the dosage of a citric acid, a pharmaceutically acceptable salt of a citric acid, or a hydrate thereof; or a mixture of the citric acid, the pharmaceutically acceptable salt of citric acid, and the hydrate thereof, which is an active component, may be a dosage at which the pH of urine (for example, early-morning urine) of a human is pH 5.2 to pH 6.8, pH 5.5 to pH 6.8, pH 5.8 to pH 6.8, pH 5.8 to pH 6.5, pH 5.8 to pH 6.2, pH 5.8 or more and less than pH 6.2, pH 6.0 to pH 6.5, pH 6.0 to pH 6.4, pH 6.0 to pH 6.3, pH 6.0 to pH 6.2, pH 6.0 or more and less than pH 6.2, pH 6.1 to pH 6.3, pH 6.2 to 6.8, pH 6.2 to pH 6.5, or pH 6.5 to 6.8, by orally administering the a citric acid, a pharmaceutically acceptable salt of a citric acid, or a hydrate thereof; or a mixture of the citric acid, the pharmaceutically acceptable salt of citric acid, and the hydrate thereof, which is an active component.

In one embodiment, the dosage of a citric acid, a pharmaceutically acceptable salt of a citric acid, or a hydrate thereof; or a mixture of the citric acid, the pharmaceutically acceptable salt of citric acid, and the hydrate thereof, which is an active component, may be a dosage at which the pH of urine (for example, early-morning urine) of a human is pH 5.2 to pH 6.8, pH 5.5 to pH 6.8, pH 5.8 to pH 6.8, pH 5.8 to pH 6.5, pH 5.8 to pH 6.2, pH 5.8 or more and less than pH 6.2, pH 6.0 to pH 6.5, pH 6.0 to pH 6.4, pH 6.0 to pH 6.3, pH 6.0 to pH 6.2, pH 6.0 or more and less than pH 6.2, pH 6.1 to pH 6.3, pH 6.2 to 6.8, pH 6.2 to pH 6.5, or pH 6.5 to 6.8 after administration for 6 weeks, 12 weeks, or 24 weeks, by orally administering the citric acid, the pharmaceutically acceptable salt of citric acid, the hydrate of the citric acid or the pharmaceutically acceptable salt, or the mixture of the citric acid, the pharmaceutically acceptable salt, or the hydrate, which is an active component.

In one embodiment, in a case where a mixture of a monohydrate of potassium citrate and a dihydrate of sodium citrate is orally administered to a human as an active component, the monohydrate of potassium citrate and the dihydrate of sodium citrate may be administered each in an amount of 0.1 to 5 g per day and in a total amount of 0.2 to 10 g per day, each in an amount of 0.1 to 3 g per day and in a total amount of 0.2 to 6 g per day, each in an amount of 0.5 to 3 g per day and in a total amount of 1 to 6 g per day, and preferably, each in an amount of 0.5 to 1.5 g per day and in a total amount of 1 to 3 g per day, each in an amount of 1 to 1.5 g per day and in a total amount of 2 to 3 g per day, or each in an amount of 0.5 to 1 g per day and in a total amount of 1 to 2 g per day, and may be divided to be administered 1 to 5, preferably 3 times per day.

In one embodiment, in a case where a monohydrate of potassium citrate or a dihydrate of sodium citrate is orally administered to a human as an active component, the monohydrate or the dihydrate may be administered at 1 to 10 g per day, 1 to 6 g per day, 2 to 5.5 g per day, 1 to 3 g per day, 2 to 3 g per day, or 1 to 1.5 g per day, and may be divided to be administered 1 to 5, preferably 3 times per day.

In one embodiment, a citric acid, a pharmaceutically acceptable salt of a citric acid, or a hydrate thereof; or a mixture of the citric acid, the pharmaceutically acceptable salt of citric acid, and the hydrate thereof, which is an active component, may be administered over a long period of time, and may be administered for, for example, 1 week, 2 weeks, 3 weeks, 6 weeks, 8 weeks, 10 weeks, 12 weeks, 24 weeks, 40 weeks, 60 weeks, 80 weeks, 100 weeks, 120 weeks, 1 week or more, 2 weeks or more, 3 weeks or more, 6 weeks or more, 8 weeks or more, 10 weeks or more, 12 weeks or more, 24 weeks or more, 40 weeks or more, 60 weeks or more, 80 weeks or more, 100 weeks or more, 120 weeks or more, 6 weeks or more and 24 weeks or less, 12 weeks or more and 24 weeks or less, 6 weeks or more and 30 weeks or less, 12 weeks or more and 30 weeks or less, 6 weeks or more and 40 weeks or less, 12 weeks or more and 40 weeks or less, 6 weeks or more and 60 weeks or less, 12 weeks or more and 60 weeks or less, 6 weeks or more and 80 weeks or less, 12 weeks or more and 80 weeks or less, 6 weeks or more and 100 weeks or less, 12 weeks or more and 100 weeks or less, 6 weeks or more and 120 weeks or less, or 12 weeks or more and 120 weeks or less.

In one embodiment, by continuous administration of the pharmaceutical composition provided by the present invention for 6 weeks, 12 weeks, and/or 24 weeks, a beneficial effect (for example, renal protection effect) can be detected in a patient with chronic kidney disease.

The chronic kidney disease (CKD) is a concept including a kidney disease that continues chronically regardless of the primary disease, and is a concept including all the pathological conditions in which there is a decrease in renal function expressed by a glomerular filtration rate (GFR), or findings suggesting kidney disorder are observed persistently and chronically (three months or more).

As shown in Clinical Practice Guidebook for Diagnosis and Treatment of Chronic Kidney Disease 2012 (The Japanese Journal of Nephrology 2012), the severity of chronic kidney disease is evaluated with the classification based on the cause (Cause: C), the renal function (GFR: G), and the proteinuria (albuminuria: A).

The categories by GFR are as follows.
G1: GFR is normal or high 90 mL/min/1.73 m$^2$)
G2: GFR is normal or mildly decreased (60 to 89 mL/min/1.73 m$^2$)
G3a: GFR is mildly to moderately decreased (45 to 59 mL/min/1.73 m$^2$)
G3b: GFR is moderately to severely decreased (30 to 44 mL/min/1.73 m$^2$)
G4: GFR is severely decreased (15 to 29 mL/min/1.73 m$^2$)
G5: end-stage kidney disease (ESKD) (<15 mL/min/1.73 m$^2$)

In a case where the primary disease is diabetes, the categories by proteinuria (albuminuria: A) are classified by using a urinary albumin/creatinine (Cr) ratio as follows.
A1: normal (less than 30 mg/gCr)
A2: microalbuminuria (30 to 299 mg/gCr)
A3: macroalbuminuria (300 mg/gCr or more)

Further, in a case where the primary disease is hypertension, nephritis, polycystic kidney disease, transplanted kidney, or the like other than diabetes, the categories by proteinuria (albuminuria: A) are classified by using a urine protein/creatinine (Cr) ratio as follows.
A1: normal (less than 0.15 g/gCr)
A2: mild proteinuria (0.15 to 0.49 g/gCr)
A3: severe proteinuria (0.50 g/gCr or more)

As shown in Clinical Practice Guidebook for Diagnosis and Treatment of Chronic Kidney Disease 2012 (The Japanese Journal of Nephrology 2012), the severity classification of chronic kidney disease (CKD) is referred to as, for example, diabetes G2A3, chronic nephritis G3bA1, or the like by using the above-described C, G, and A.

However, the severity of chronic kidney disease has conventionally been expressed only by the stages classified by GFR, and in consideration of this circumstance, the severity of chronic kidney disease can also be expressed by the stages of G1, G2, G3a, G3b, G4, and G5 as in the past.

In one embodiment, the pharmaceutical composition provided by the present invention is administered to a patient with less severe early-stage chronic kidney disease.

In one embodiment, the pharmaceutical composition provided by the present invention is administered to a patient with chronic kidney disease of stage G3b or less, preferably stage G2 or less.

In one embodiment, the pharmaceutical composition provided by the present invention is administered to a patient with chronic kidney disease of stage G2 or more and G3b or less (for example, stage G2 and stage G3a; or stage G2, stage G3a, and stage G3b).

In one embodiment, the pharmaceutical composition provided by the present invention is administered to a patient with chronic kidney disease of stage G3b or less and microalbuminuria, and preferably to a patient with chronic kidney disease of stage G2 and microalbuminuria.

In one embodiment, the pharmaceutical composition provided by the present invention is administered to a patient with chronic kidney disease of stage G2 or more and G3b or less (for example, stage G2 and stage G3a; or stage G2, stage G3a, and stage G3b) and microalbuminuria.

In one embodiment, the pharmaceutical composition provided by the present invention is administered to a patient with chronic kidney disease of stage G3b or less having a urinary protein excretion of less than 3.5 g/gCr, and preferably to a patient with chronic kidney disease of stage G2 having a urinary protein excretion of less than 3.5 g/gCr.

In one embodiment, the pharmaceutical composition provided by the present invention is administered to a patient with chronic kidney disease of stage G2 or more and G3b or less (for example, stage G2 and stage G3a; or stage G2, stage G3a, and stage G3b) having a urinary protein excretion of less than 3.5 g/gCr.

In one embodiment, the pharmaceutical composition provided by the present invention is administered to a patient with progressive chronic kidney disease.

In one embodiment, the pharmaceutical composition provided by the present invention is administered to a patient with chronic kidney disease with hypertension.

In one embodiment, the pharmaceutical composition provided by the present invention is administered to a patient to be treated in accordance with Clinical Practice Guidebook for Diagnosis and Treatment of Chronic Kidney Disease. For example, the pharmaceutical composition is administered to a patient to be subjected to blood pressure management (for example, administration of a renin-angiotensin (RA) system inhibitor such as an angiotensin receptor blocker (ARB) or an angiotensin-converting enzyme (ACE) inhibitor, a diuretic agent, or a Ca antagonist), proteinuria measures (for example, administration of a renin-angiotensin (RA) system inhibitor), blood glucose level management (for example, administration of an α-glucosidase inhibitor), lipid management (for example, administration of statin, or fibrate), anemia management (for example, administration of erythropoietin), and/or bone and mineral measures (for example, administration of bisphosphonate, in accordance with Clinical Practice Guidebook for Diagnosis and Treatment of Chronic Kidney Disease).

In one embodiment, the pharmaceutical composition provided by the present invention is used in combination with an antihypertensive agent (such as an ARB, an ACE inhibitor, a diuretic agent, or a Ca antagonist).

In one embodiment, the pharmaceutical composition provided by the present invention is used in combination with spherical absorbing carbon obtained by oxidizing and reducing spherical fine porous carbon derived from a petroleum-based hydrocarbon at a high temperature (KREMEZIN (registered trademark) available on the market in Japan).

Examples of another embodiment of the present invention include:

1-1) A method for renal protection in a mammalian subject (for example, human) suffering from chronic kidney disease, including administering to a subject in need of the renal protection an effective amount of a citric acid, a pharmaceutically acceptable salt of a citric acid, or a hydrate thereof; or a mixture of the citric acid, the pharmaceutically acceptable salt of citric acid, and the hydrate thereof;

1-2) A method for suppression of acidosis or improvement of aciduria, with chronic kidney disease in a mammalian subject (for example, human), including administering to a subject in need of suppression of the acidosis with chronic kidney disease an effective amount of a citric acid, a pharmaceutically acceptable salt of a citric acid, or a hydrate thereof; or a mixture of the citric acid, the pharmaceutically acceptable salt of citric acid, and the hydrate thereof, with which RAS activation is suppressed in the kidney of the subject;

1-3) A method for suppression of oxidative stress in the kidney in a mammalian subject (for example, human) suffering from chronic kidney disease, including administering to a subject in need of suppression of the oxidative stress an effective amount of a citric acid, a pharmaceutically acceptable salt of a citric acid, or a hydrate thereof; or a mixture of the citric acid, the pharmaceutically acceptable salt of citric acid, and the hydrate thereof;

1-4) A method for determination of glomerular filtration function in a mammalian subject (for example, human), including administering to a subject in need of determination of the glomerular filtration function an effective amount of a pharmaceutical composition containing a citric acid, a pharmaceutically acceptable salt of a citric acid, or a hydrate thereof; or a mixture of the citric acid, the pharmaceutically acceptable salt of citric acid, and the hydrate thereof, measuring the pH of urine before and after the administration, and calculating the difference between the pH of urine after the administration and the pH of urine before the administration (for example, when the difference is −1 or less, the eGFR is determined to be less than 50, and when the difference is 1 or more, the eGFR is determined to be 50 or more);

2-1) A pharmaceutical composition containing a citric acid, a pharmaceutically acceptable salt of a citric acid, or a hydrate thereof; or a mixture of the citric acid, the pharmaceutically acceptable salt of citric acid, and the hydrate thereof, for use in renal protection in a mammalian subject (for example, human) suffering from chronic kidney disease;

2-2) A pharmaceutical composition containing a citric acid, a pharmaceutically acceptable salt of a citric acid, or a hydrate thereof; or a mixture of the citric acid, the pharmaceutically acceptable salt of citric acid, and the hydrate thereof, for use in suppression of intrarenal RAS activation, and suppression of acidosis or improvement of aciduria with chronic kidney disease;

2-3) A pharmaceutical composition containing a citric acid, a pharmaceutically acceptable salt of a citric acid, or a hydrate thereof; or a mixture of the citric acid, the pharmaceutically acceptable salt of citric acid, and the hydrate thereof, for use in suppression of oxidative stress in the kidney of a mammalian subject (for example, human) suffering from chronic kidney disease;

2-4) A pharmaceutical composition containing a citric acid, a pharmaceutically acceptable salt of a citric acid, or a hydrate thereof; or a mixture of the citric acid, the pharmaceutically acceptable salt of citric acid, and the hydrate thereof, for use in determination of glomerular filtration function;

3-1) Use of a citric acid, a pharmaceutically acceptable salt of a citric acid, or a hydrate thereof; or a mixture of the citric acid, the pharmaceutically acceptable salt of citric acid, and the hydrate thereof, for production of a pharmaceutical composition for renal protection in a mammalian subject (for example, human) suffering from chronic kidney disease;

3-2) Use of a citric acid, a pharmaceutically acceptable salt of a citric acid, or a hydrate thereof; or a mixture of the citric acid, the pharmaceutically acceptable salt of citric acid, and the hydrate thereof, for production of a pharmaceutical composition for suppression of intrarenal RAS activation and for suppression of acidosis or improvement of aciduria with chronic kidney disease;

3-3) Use of a citric acid, a pharmaceutically acceptable salt of a citric acid, or a hydrate thereof; or a mixture of the citric acid, the pharmaceutically acceptable salt of citric acid, and the hydrate thereof, for production of a pharmaceutical composition for suppression of oxidative stress in the kidney of a mammalian subject (for example, human) suffering from chronic kidney disease; and 3-4) Use of a citric acid, a pharmaceutically acceptable salt of a citric acid, or a hydrate thereof; or a mixture of the citric acid, the pharmaceutically acceptable salt of citric acid, and the hydrate thereof, for production of a pharmaceutical composition for determination of glomerular filtration function.

2. Food Composition

In one embodiment, a food composition provided by the present invention contains a citric acid, a pharmaceutically acceptable salt of a citric acid, or a hydrate thereof; or a mixture of the citric acid, the pharmaceutically acceptable salt of citric acid, and the hydrate thereof, and exerts an effect of protecting the kidney or maintaining the kidney health.

In one embodiment, the food composition provided by the present invention exerts an effect of suppressing oxidative stress in the kidney.

As the active component, the active components described in "1. Pharmaceutical composition" can be applied. For example, the food composition provided by the present invention can be a food composition containing an alkali metal salt of citric acid or a hydrate thereof, or a mixture of the alkali metal salt or the hydrate, and preferably a mixture of a monohydrate of potassium citrate ($C_6H_5K_3O_7 \cdot H_2O$) and a dihydrate of sodium citrate ($C_6H_5Na_3O_7 \cdot 2H_2O$).

The content of a citric acid, a pharmaceutically acceptable salt of a citric acid, or a hydrate thereof; or a mixture of the citric acid, the pharmaceutically acceptable salt of citric acid, and the hydrate thereof, in the food composition provided by the present invention can be appropriately determined depending on the kind of food. Examples of the food composition include a food for specified health uses, a food with function claims, a food for hospital patients, and a supplement. The form of such a food composition is not particularly limited as long as the food composition contains a citric acid, a pharmaceutically acceptable salt of a citric acid, or a hydrate thereof; or a mixture of the citric acid, the pharmaceutically acceptable salt of citric acid, and the hydrate thereof in an amount effective for exerting the effects described above, and is in an orally ingestible form, and the food composition may be in a form of ordinary food and drink, or may be provided as a preparation suitable for oral administration, for example, a preparation such as a tablet, a capsule, or a suspension, among the preparations that can be applied to the pharmaceutical composition. As to the formulation and production method of such a preparation, in the present specification, the formulation and production method of a pharmaceutical preparation described in "1. Pharmaceutical composition" can be applied as they are, and further a preparation technique known per se in the technical field of pharmaceutical preparation can be applied.

For example, in a case of a food for specified health uses, a food with function claims, a food for hospital patients, or a supplement, such a food or a supplement may contain a monohydrate of potassium citrate and a dihydrate of sodium citrate in a total amount of ⅓ of 1 to 3 g as active components, or sodium bicarbonate in an amount of ⅓ of 1 to 6 g as an active component, per meal of the food or the supplement. In a case where a food for specified health uses, a food with function claims, a food for hospital patients, or a supplement is provided as tablets, such a food or a supplement may contain, for example, a citric acid, a pharmaceutically acceptable salt of a citric acid, or a hydrate thereof; or a mixture of the citric acid, the pharmaceutically acceptable salt of citric acid, and the hydrate thereof in an amount of 70 to 80% by weight, per tablet of 300 mg to 600 mg.

In a case where the food composition provided by the present invention is not formulated and is provided in a form of ordinary food and drink, such a food and drink can be appropriately produced by a person skilled in the art depending on the kind of the food, and for example, can be produced by mixing a citric acid, a pharmaceutically acceptable salt of a citric acid, or a hydrate thereof; or a mixture of the citric acid, the pharmaceutically acceptable salt of citric acid, and the hydrate thereof, in a food material.

Examples of the form of such a food and drink include a liquid, emulsified, or pasty food such as a beverage, soy sauce, milk, yogurt, or miso (fermented soybean paste); a semisolid food such as jelly, or gummy candy; a solid food such as candy, gum, tofu (soybean curd), or a supplement; and a powdery food.

Examples of the beverage include a fruit juice/fruit beverage, a coffee beverage, an oolong tea beverage, a green tea beverage, a black tea beverage, a barley tea beverage, a vegetable beverage, a carbonated beverage being a soft drink, a fruit extract-containing beverage, a vegetable extract-containing juice, near water (soft drink with minute amounts of flavoring, etc.), a sports beverage, and a diet beverage.

Into such a beverage, an additive agent such as an antioxidant, a flavor, various kinds of esters, an organic acid, an organic acid salt, an inorganic acid, an inorganic acid salt, an inorganic salt, a dyestuff, an emulsifier, a preservative, a seasoning, a sweetener, an acidulant, a fruit juice extract, a vegetable extract, a nectar extract, a pH adjusting agent, or a quality stabilizer can be added alone or in combination thereof.

The term "administration" described in "1. Pharmaceutical composition" can be applied also to the "food composition" according to the present invention, and further, the term "administration" can be replaced with "ingestion" in the "food composition" according to the present invention. Accordingly, for example, the term "administer", "administered", or the like can be replaced with "allowing . . . to ingest", "ingest", "ingested", or the like while inflecting the word depending on the context.

Therefore, examples of the embodiment of the food composition according to the present invention include the following ones.

<1> A food composition for maintaining kidney health, containing a citric acid, a pharmaceutically acceptable salt of a citric acid, or a hydrate thereof; or a mixture of the citric acid, the pharmaceutically acceptable salt of citric acid, and the hydrate thereof;

<11> A method for maintaining kidney health, which is a method for allowing a subject in need of maintaining the kidney health to ingest a food composition containing an effective amount of a citric acid, a pharmaceutically acceptable salt of a citric acid, or a hydrate thereof; or a mixture of the citric acid, the pharmaceutically acceptable salt of citric acid, and the hydrate thereof; and <111> Use of citric acid, a pharmaceutically acceptable salt of a citric acid, a pharmaceutically acceptable salt of a citric acid, or a hydrate thereof; or a mixture of the citric acid, the pharmaceutically acceptable salt of citric acid, and the hydrate thereof, for production of a food composition for maintaining kidney health.

It is preferred that effects of maintaining kidney health and the like are displayed on the packaging, container, or instructions of the food composition according to the present invention.

Other examples of the embodiment of the present invention include:

(1)

A pharmaceutical composition for renal protection in chronic kidney disease, containing a citric acid, a pharmaceutically acceptable salt of a citric acid, or a hydrate thereof; or a mixture of the citric acid, the pharmaceutically acceptable salt of citric acid, and the hydrate thereof;

(2)

The pharmaceutical composition described in (1), which protects renal tissues;

(3)

The pharmaceutical composition described in (1) or (2), which maintains or improves renal function;

(4)

The pharmaceutical composition described in any one of (1) to (3), which protects renal tubular tissues;

(5)

The pharmaceutical composition described in any one of (1) to (4), which maintains or improves renal tubular function;

(6)

The pharmaceutical composition described in any one of (1) to (5), which maintains or improves urinary concentrating capacity;

(7)

The pharmaceutical composition described in any one of (1) to (6), which suppresses oxidative stress in the kidney;

(8)

A pharmaceutical composition for treatment or prevention of acidosis or for improvement of aciduria in chronic kidney disease with hypertension, containing citric acid, a pharmaceutically acceptable salt of citric acid, a hydrate of the citric acid or the pharmaceutically acceptable salt, or a mixture of the citric acid, the pharmaceutically acceptable salt, or the hydrate;

(9)

The pharmaceutical composition described in any one of (1) to (8), in which the mixture of the citric acid, the pharmaceutically acceptable salt of the citric acid, or the hydrate thereof; or a mixture of the citric acid, the pharmaceutically acceptable salt of citric acid, and the hydrate thereof;

(10)

The pharmaceutical composition described in any one of (1) to (9), further containing anhydrous citric acid;

(11)

The pharmaceutical composition described in any one of (1) to (10), in which the citric acid, the pharmaceutically acceptable salt of citric acid, the hydrate of the citric acid or the pharmaceutically acceptable salt, or the mixture of the citric acid, the pharmaceutically acceptable salt, or the hydrate is administered at 1 to 3 g per day;

(12)

The pharmaceutical composition described in any one of (1) to (11), in which the citric acid, the pharmaceutically acceptable salt of citric acid, the hydrate of the citric acid or the pharmaceutically acceptable salt, or the mixture of the citric acid, the pharmaceutically acceptable salt, or the hydrate is administered at 1 to 1.5 g per day;

(13)

The pharmaceutical composition described in any one of (1) to (12), which is administered to a patient with chronic kidney disease of stage G2 or more and G3b or less;

(14)

The pharmaceutical composition described in any one of (1) to (13), in which the citric acid, the pharmaceutically acceptable salt of citric acid, the hydrate of the citric acid or the pharmaceutically acceptable salt, or the mixture of the citric acid, the pharmaceutically acceptable salt, or the hydrate is administered for 6 weeks or more;

(15)

A pharmaceutical composition for renal function diagnosis, containing citric acid, a pharmaceutically acceptable a citric acid, a pharmaceutically acceptable salt of a citric acid, or a hydrate thereof; or a mixture of the citric acid, the pharmaceutically acceptable salt of citric acid, and the hydrate thereof;

(16)

The pharmaceutical composition described in (15), in which the renal function is a glomerular filtration function;

(17)

The pharmaceutical composition described in (15) or (16), which is administered to a patient with chronic kidney disease, and is a pharmaceutical composition for renal function diagnosis in the patient with chronic kidney disease;

(18)

The pharmaceutical composition described in any one of (15) to (17), in which the mixture of the citric acid, the pharmaceutically acceptable salt of the citric acid, or the hydrate thereof; or a mixture of the citric acid, the pharmaceutically acceptable salt of citric acid, and the hydrate thereof;

(19)

The pharmaceutical composition described in any one of (15) to (18), further containing anhydrous citric acid;

(20)

The pharmaceutical composition described in any one of (15) to (19), in which the citric acid, the pharmaceutically acceptable salt of citric acid, the hydrate of the citric acid or the pharmaceutically acceptable salt, or the mixture of the citric acid, the pharmaceutically acceptable salt, or the hydrate is administered at 1 to 3 g per day;

(21)

The pharmaceutical composition described in any one of (15) to (20), in which the citric acid, the pharmaceutically acceptable salt of citric acid, the hydrate of the citric acid or the pharmaceutically acceptable salt, or the mixture of the citric acid, the pharmaceutically acceptable salt, or the hydrate is administered at 1 to 1.5 g per day;

(22)

The pharmaceutical composition described in any one of (15) to (21), which is administered to a patient with chronic kidney disease of stage G2 or more and G3b or less;

(23)

A medical kit for renal function diagnosis, including the pharmaceutical composition described in any one of (15) to (22), and a test paper for measuring a pH of a human urine;

(24)

A method for determining a renal function, including administering the pharmaceutical composition described in any one of (15) to (22) to a subject, and measuring a pH of urine of the subject after the administration;

(25)

The method described in (24), in which the urine of the subject after the administration is a urine collected from the subject for the first time after the administration;

(26)

The method described in (24) or (25), in which the urine of the subject after the administration is a urine collected from the subject after the lapse of 2 to 5 hours from the administration;

(27)

The method described in any one of (24) to (26), in which the subject is a patient with chronic kidney disease to which a pharmaceutical composition containing an alkaline agent has been continuously administered;

(28)

The method described in any one of (24) to (27), in which the subject is a patient with chronic kidney disease to which a pharmaceutical composition containing an alkaline agent has been continuously administered, and in a case where a pH value of urine of the subject after administration of the pharmaceutical composition described in any one of (15) to (22) after the continuous administration of the alkaline agent is higher than a pH value of urine of the subject after administration of the pharmaceutical composition described in any one of (15) to (22) before the continuous administration of the alkaline agent, the subject is determined to have improved renal function;

(29)

A method for determining a renal function, including administering the pharmaceutical composition described in any one of (15) to (22) to a subject, and measuring a pH of early-morning urine of the subject before the administration and a pH of urine of the subject after the administration;

(30)

The method described in (29), in which the early-morning urine of the subject before the administration is an early-morning urine collected from the subject for the last time before the administration;

(31)

The method described in (29) or (30), in which the urine of the subject after the administration is an early-morning urine collected from the subject by 3 hours before the administration;

(32)

The method described in any one of (29) to (31), in which the urine of the subject after the administration is a urine collected from the subject for the first time after the administration;

(33)

The method described in any one of (29) to (32), in which the urine of the subject after the administration is a urine collected from the subject after the lapse of 2 to 5 hours from the administration;

(34)

The method described in any one of (29) to (33), in which the subject is a patient with chronic kidney disease to which a pharmaceutical composition containing an alkaline agent has been continuously administered;

(35)

The method described in any one of (29) to (34), in which the subject is a patient with chronic kidney disease to which a pharmaceutical composition containing an alkaline agent has been continuously administered, and in a case where when comparing a pH value after the continuous administration with a pH value before continuous the administration, the difference obtained by subtracting a pH value of early-morning urine of the subject before administration of the pharmaceutical composition described in any one of (15) to (22) from a pH value of urine of the subject after administration of the pharmaceutical composition described in any one of (15) to (22) is large, the subject is determined to have improved renal function;

(36)

The method described in any one of (29) to (35), in which in a case where the difference obtained by subtracting a pH value of early-morning urine of the subject before administration of the pharmaceutical composition described in any one of (15) to (22) from a pH value of urine of the subject after administration of the pharmaceutical composition described in any one of (15) to (22) is −1 or less, the subject is determined to have an eGFR of less than 50; and (37)

The method described in any one of (29) to (36), in which in a case where the difference obtained by subtracting a pH value of early-morning urine of the subject before administration of the pharmaceutical composition described in any one of (15) to (22) from a pH value of urine of the subject after administration of the pharmaceutical composition described in any one of (15) to (22) is 1 or more, the subject is determined to have an eGFR of 50 or more.

Hereinafter, the present invention is further described by way of Examples, however, the present invention is not limited to the Examples.

EXAMPLES

A clinical trial in humans was conducted to examine the effects by oral administration of a potassium citrate/sodium citrate hydrate preparation and a sodium bicarbonate preparation, which are oral alkaline agents.

1. Method 93 patients with chronic kidney disease of stage G2 to G3b (eGFR: 30 to 89 ml/min/1.73 m$^2$) were randomly divided into an administration group of a potassium citrate/sodium citrate hydrate preparation (group A: 31 patients), an administration group of a sodium bicarbonate preparation (group B: 31 patients), and a control group (group C: 31 patients). The patients were allocated to respective groups so that the age, the sex, the presence or absence of diabetes, and the eGFR were balanced. In each group, a treatment based on "Clinical Practice Guidebook for Diagnosis and Treatment of Chronic Kidney Disease—Summary of treatment" (hereinafter, referred to as "standard of care") was performed.

An alkaline agent was not administered to the control group. In the group A, three tablets, each containing 231.5 mg of potassium citrate ($C_6H_5K_3O_7 \cdot H_2O$) and 195.0 mg of sodium citrate hydrate ($C_6H_5Na_3O_7 \cdot 2H_2O$) were divided to be orally administered 3 times (morning, daytime, and evening) per day for 24 weeks. In this regard, the pH of early-morning urine was controlled over time, and in a case where the pH of early-morning urine was less than 6.5, the dosage was able to be increased up to 6 tablets per day, 3 times (morning, daytime, and evening) per day as appropriate at the discretion of a doctor. In the group B, three tablets, each containing 500 mg of sodium bicarbonate were divided to be orally administered 3 times (morning, daytime, and evening) per day for 24 weeks. In this regard, the pH of early-morning urine was controlled over time, and in a case where the pH of early-morning urine was less than 6.5, the dosage was able to be increased up to 6 tablets per day, 3 times (morning, daytime, and evening) per day as appropriate at the discretion of a doctor.

Early-morning urine, spot urine, and blood were collected before the start of administration and after administration for 6 weeks, 12 weeks, and 24 weeks, and the collected samples were stored at −80° C.

The 8-OHdG concentration and angiotensinogen concentration in urine were measured by an enzyme-linked immunosorbent assay (ELISA).

The iron concentration in serum was measured by nitroso-PSAP method, and the ferritin concentration was measured by a chemiluminescent enzyme immunoassay (CLEIA) method.

The amount of β2-microglobulin in urine was measured by a latex agglutination immunoassay using LZ Test Eiken β2-M and LZ-β2-M Standard U Eiken (EIKEN CHEMICAL CO., LTD., Tokyo, Japan).

The osmotic pressure of urine was measured by a freezing point depression method.

The albumin concentration and protein concentration in urine were measured by using an immunoturbidimetric method, and a colorimetric method.

The creatinine concentration in urine was measured by an enzyme method.

As to the statistical analysis, the Mann-Whitney test was used for comparison among groups, and the Wilcoxon test was used for comparison of the changes over time. Further, the Pearson test was used for the correlation.

2. Results

From the measurement results, for each patient in group A (administration group of a potassium citrate/sodium citrate hydrate preparation), group B (administration group of a sodium bicarbonate preparation), and group C (control group), the following values were calculated.

(i) A value obtained by dividing each concentration of 8-OHdG and angiotensinogen in early-morning urine before the start of administration by the urinary creatinine concentration (ii) A value obtained by dividing each concentration of 8-OHdG and angiotensinogen in early-morning urines after administration for 6 weeks, 12 weeks, and 24 weeks by the urinary creatinine concentration (iii) A ratio of the value obtained by dividing each concentration of 8-OHdG in early-morning urines after administration for 6 weeks, 12 weeks, and 24 weeks by the urinary creatinine concentration to the value obtained by dividing each concentration of 8-OHdG in early-morning urine before the start of administration by the urinary creatinine concentration (the value obtained by dividing each concentration of 8-OHdG in early-morning urines after administration for 6 weeks, 12 weeks, and 24 weeks by the urinary creatinine concentration/the value obtained by dividing each concentration of 8-OHdG in early-morning urine before the start of administration by the urinary creatinine concentration)

(iv) A value obtained by dividing each concentration of $\beta_2$-microglobulin and albumin in early-morning urine before the start of administration by the urinary creatinine concentration (v) A value obtained by dividing each concentration of $\beta_2$-microglobulin and albumin in early-morning urines after administration for 6 weeks, 12 weeks, and 24 weeks by the urinary creatinine concentration (vi) The difference obtained by subtracting a value obtained by dividing each concentration of $\beta_2$-microglobulin and albumin in early-morning urine before the start of administration by the urinary creatinine concentration from a value obtained by dividing each concentration of $\beta_2$-microglobulin and albumin in early-morning urines after administration for 6 weeks, 12 weeks, and 24 weeks by the urinary creatinine concentration (the value obtained by dividing each concentration of $\beta_2$-microglobulin and albumin in early-morning urines after administration for 6 weeks, 12 weeks, and 24 weeks by the urinary creatinine concentration–the value obtained by dividing each concentration of β2-microglobulin and albumin in early-morning urine before the start of administration by the urinary creatinine concentration)

(vii) A value obtained by dividing each concentration of albumin and protein in spot urine before the start of administration by the urinary creatinine concentration (viii) A value obtained by dividing each concentration of albumin and protein in early-morning urines after administration for 6 weeks, 12 weeks, and 24 weeks by the urinary creatinine concentration (ix) The difference obtained by subtracting a value obtained by dividing each concentration of albumin and protein in early-morning urine before the start of administration by the urinary creatinine concentration from a value obtained by dividing each concentration of albumin and protein in early-morning urines after administration for 6 weeks, 12 weeks, and 24 weeks by the urinary creatinine concentration (the value obtained by dividing each concentration of albumin and protein in early-morning urines after administration for 6 weeks, 12 weeks, and 24 weeks by the urinary creatinine concentration—the value obtained by dividing each concentration of albumin and protein in early-morning urine before the start of administration by the urinary creatinine concentration)

(x) An osmotic pressure value of early-morning urine before the start of administration (xi) Each osmotic pressure value of early-morning urines after administration for 6 weeks, 12 weeks, and 24 weeks Further, for the above (i) to (xii), the average value and standard deviation (SD) of each group were calculated.

The results are shown in the following Tables. In this regard, in Tables and Drawings, group A, which is an administration group of a potassium citrate/sodium citrate hydrate preparation, is referred to as "Citrate", and group B, which is an administration group of a sodium bicarbonate preparation, is referred to as "Bicarbonate".

Table 1 shows ratios (%) of a value obtained by dividing each concentration of 8-OHdG in early-morning urines after administration for 6 weeks, 12 weeks, and 24 weeks by the urinary creatinine concentration to a value obtained by dividing each concentration of 8-OHdG in early-morning urine before the start of administration by the urinary creatinine concentration.

TABLE 1

| | | Urine 8-OHdG (μg/gCr, % Relative value vs 0 Week) | | | |
|---|---|---|---|---|---|
| Group | N | 6 W | 12 W | 24 W | 6-24 $W^j$ (89-91) |
| Control | 30 | 98 ± 35$^{h,r}$ | 101 ± 35$^f$ | 100 ± 53$^d$ | 100 ± 41$^{b,a}$ |
| Citrate | 27-30 | 90 ± 34$^{i,n}$ | 90 ± 41$^{g,q}$ | 82 ± 32$^{e,p}$ | 87 ± 36$^{a,c,o}$ |
| Bicarbonate | 27-29 | 106 ± 16 | 110 ± 23 | 105 ± 27 | 107 ± 23 |

Mean ± SD $^a$p = 0.0126 vs $^b$p = 0.0005, $^c$p < 0.0001, $^d$p = 0.0917, $^e$p = 0.0003, $^f$p = 0.0177, $^g$p = 0.0062, $^h$p = 0.0263, $^i$p = 0.0003 vs Bicarbonate (Mann-Whitney) $^j$p < 0.0001, $^k$p = 0.0031, $^l$p = 0.0070, $^m$p = 0.0023 (Kruskal-Wallis) and $^n$p = 0.0014, $^o$p < 0.0001, $^p$p = 0.0021, $^q$p = 0.0005, $^r$p = 0.0636, $^s$p = 0.0018 vs Bicarbonate (Dunn)

In group A (Citrate, an administration group of a potassium citrate/sodium citrate hydrate preparation), the value of each concentration of 8-OHdG in early-morning urines after administration for 6 weeks, 12 weeks, and 24 weeks was lower than those in group B (Bicarbonate, an administration group of a sodium bicarbonate preparation) and group C (Control, a control group) (see Table 1). In group A, each concentration of 8-OHdG in early-morning urines after administration for 6 to 24 weeks was significantly decreased as compared with those in groups B and C (see Table 1). The 8-OHdG concentration in urine reflects the accumulation of 8-OHdG in the kidney, which is an indicator of tissue damage. From the above results, it was indicated that the administration of a potassium citrate/sodium citrate hydrate preparation was useful for suppression of oxidative stress in the kidney of a patient with chronic kidney disease, and by the administration of a potassium citrate/sodium citrate hydrate preparation a renal tissue protection effect was exerted.

Table 2 shows values (µg/gCr) obtained by dividing each amount of angiotensinogen in early-morning urines before the start of administration and after administration for 6 weeks, 12 weeks, 24 weeks, and 6 to 24 weeks by the urinary creatinine concentration.

TABLE 2

| Urine Angiotensinogen (g/gCr) | | | | | | |
|---|---|---|---|---|---|---|
| Group | N | 0 W | 6 W | 12 W | 24 W | 6-24 W$^a$(87-89) |
| Control | 28-29 | 16.4 ± 22.9 | 15.4 ± 20.9 | 17.2 ± 31.0 | 20.7 ± 34.7 | 17.8 ± 29.2$^a$ |
| Citrate | 29-31 | 17.2 ± 31.0 | 20.5 ± 42.6$^d$ | 17.9 ± 26.5 | 14.1 ± 23.5$^c$ | 17.5 ± 31.8 |
| Bicarbonate | 27-31 | 15.7 ± 18.2 | 19.7 ± 23.3 | 22.8 ± 38.9 | 22.8 ± 38.9 | 21.7 ± 31.5 |

Mean +/− SD
$^a$p = 0.0792,
$^b$p = 0.0166,
$^c$p = 0.0984 and
$^d$p = 0.0780 vs Bicarbonate (Mann-Whitney)
Not significant vs 0 week (Wilcoxon)
$^e$p = 0.0495 (Kruskal-Wallis) and
$^f$p = 0.0596 vs Bicarbonate (Dunn)
(No significant difference among groups in week 0)

In group B (Bicarbonate, an administration group of a sodium bicarbonate preparation), each concentration of angiotensinogen in early-morning urines after administration for 6 to 24 weeks was significantly higher than that in group A (Citrate, an administration group of a potassium citrate/sodium citrate hydrate preparation) (see Table 2). It was indicated that the administration of sodium bicarbonate acted in a direction to enhance the intrarenal renin-angiotensin system, but in contrast, the administration of a potassium citrate/sodium citrate hydrate preparation exerted no such an action.

Table 3 shows differences (µg/gCr) obtained by subtracting a value obtained by dividing each concentration of $\beta_2$-microglobulin in early-morning urine before the start of administration by the urinary creatinine concentration from a value obtained by dividing each concentration of $\beta_2$-microglobulin in early-morning urines after administration for 6 weeks, 12 weeks, and 24 weeks by the urinary creatinine concentration.

TABLE 3

| Urine $\beta_2$-microglobulin (µg/gCr, Δ Measured value vs 0 Week) | | | | | |
|---|---|---|---|---|---|
| Group | N | 6 W | 12 W | 24 W | 6-24 W (89-91) |
| Control | 26-27 | 58.9 ±171.4 (21.5) | 82.4 ±188.4 (34.5) | 80.5 ±215.8 (14.0) | 74.0 ±190.9 (28.0) |
| Citrate | 28-29 | −12.9 ±125.5$^b$ (−7.0) | 40.7 ±260.2 (15.0) | 87.3 ±362.7 (23.0) | 37.8 ±206.4$^a$ (7.0) |
| Bicarbonate | 26-29 | 38.6 ±189.9 (8.0) | 82.2 ±226.3 (10.0) | 60.1 ±157.2 (27.0) | 61.4 ±191.8 (14.0) |

Mean ± SD ( ): Median
$^a$p = 0.0818 and $^b$p = 0.0615 vs Control (Mann-Whitney)
Not Significant between Groups (Kruskal-Wallis & Dunn)

In group A (Citrate, an administration group of a potassium citrate/sodium citrate hydrate preparation), it was observed that each concentration of $\beta_2$-microglobulin in early-morning urines after administration for 6 to 24 weeks tended to be lower as compared with that in group C (Control, control group) (see Table 3). Such a tendency was not observed in group B (Bicarbonate, an administration group of a sodium bicarbonate preparation) (see Table 3). It was suggested that the administration of a potassium citrate/sodium citrate hydrate preparation exerted a protection effect on renal tubular tissues as compared with that in the control group.

Table 4 shows differences (mg/gCr) obtained by subtracting a value obtained by dividing each concentration of albumin in early-morning urine before the start of administration by the urinary creatinine concentration from a value obtained by dividing each concentration of albumin in early-morning urines after administration for 6 weeks, 12 weeks, and 24 weeks by the urinary creatinine concentration.

urine after the administration tended to become lower as compared with that before the start of administration. Such a tendency was not observed in group B (Bicarbonate, an administration group of a sodium bicarbonate preparation) and in group C (Control, control group) (see Table 4).

Further, in group A (Citrate, an administration group of a potassium citrate/sodium citrate hydrate preparation), each albumin concentration in early-morning urines after administration for 6 to 24 weeks was significantly lower than those in group B (Bicarbonate, an administration group of a sodium bicarbonate preparation) and group C (Control, a control group) (see Table 4). It was indicated that the renal function was protected by the administration of a potassium citrate/sodium citrate hydrate preparation.

Table 5 shows differences (mg/gCr) obtained by subtracting a value obtained by dividing each concentration of albumin in spot urine before the start of administration by the urinary creatinine concentration from a value obtained

TABLE 4

Early Morning Urine Albumin (mg/gCr, Δ Measured value vs 0 Week)

| Group | N | 6 W | 12 W | 24 W | 6-24 W$^a$ (88-91) |
|---|---|---|---|---|---|
| Control | 30-31 | 19.6 ±102 | -2.0 ±132 | 34.1 ± 151 | 17.4 ± 180 |
|  |  | (-0.98) | (-0.68) | (0.72) | (-0.47) |
| Citrate | 29-31 | -18.3 ± 99 | -25.4 ±91$^d$ | -12.8 ±59$^{a,e}$ | -18.8 ±84$^{b,f,g}$ |
|  |  | (-0.07) | (-1.07) | (-2.12) | (-0.98) |
| Bicarbonate | 27-31 | 26.9 ±123 | 51.3 ±148 | 50.7 ± 136 | 43.6 ± 186 |
|  |  | (-0.53) | (0.55) | (0.97) | (0.74) |

Mean ± SD ( ): Median $^a$p = 0.0508 vs Control and $^b$p = 0.0108, $^c$p = 0.0256, $^d$p = 0.0951 vs Bicarbonate (Mann-Whitney) $^e$p = 0.0353 (Kruskal-Wallis) and $^f$p = 0.0292 vs Bicarbonate (Dunn) $^g$p = 0.0272 vs Control (Student-t)

In group A (Citrate, an administration group of a potassium citrate/sodium citrate hydrate preparation), it was observed that the albumin concentration in early-morning by dividing each concentration of albumin in spot urines after administration for 6 weeks, 12 weeks, and 24 weeks by the urinary creatinine concentration.

TABLE 5

Spot Urine Albumin (mg/gCr, Δ Measured value vs 0 Week)

| Group | N | 6 W | 12 W | 24 W$^g$ | 6-24 W$^{b,j}$ (85-91) |
|---|---|---|---|---|---|
| Control | 30-31 | 45.7 ±188 | 88.7 ± 185 | 69.8 ± 141 | 48.2 ± 171$^b$ |
|  |  | (-1.1) | (34.5) | (0.5) | (0.8) |
| Citrate | 29-31 | -10.4 ±175 | -32.2 ±199$^e$ | -16.2 ±169$^{a,i,k}$ | -19.5 ±180$^{c,b,j,m}$ |
|  |  | (0.2) | (0) | (-2.4) | (7.0) |
| Bicarbonate | 26-29 | 40.2 ±126 | 72.5 ± 243 | 121 ± 261 | 79.0 ± 221 |
|  |  | (4.9) | (7.15) | (9.2) | (8.0) |

Mean ± SD ( ): Median $^a$p = 0.0751 vs Control and $^b$p = 0.0258, $^c$p = 0.0005, $^d$p = 0.0097, $^e$p = 0.0741 vs Bicarbonate (Mann-Whitney) $^f$p = 0.0018, $^g$p = 0.0226 (Kruskal-Wallis) and $^h$p = 0.0010, $^i$p = 0.0185 vs Bicarbonate (Dunn) $^j$p = 0.0101 and $^k$p = 0.0635 vs Control (Student-t) $^l$p = 0.0025 (1 way ANOVA) and $^m$p = 0.0467 vs Control (Tukey)

In group A (Citrate, an administration group of a potassium citrate/sodium citrate hydrate preparation), it was observed that the albumin concentration in spot urine after the administration tended to become lower as compared with that before the start of administration. Such a tendency was not observed in group B (Bicarbonate, an administration group of a sodium bicarbonate preparation) and in group C (Control, control group) (see Table 5).

Further, in group A (Citrate, an administration group of a potassium citrate/sodium citrate hydrate preparation), each albumin concentration in early-morning urines after administration for 6 to 24 weeks was lower than those in group B (Bicarbonate, an administration group of a sodium bicarbonate preparation) and group C (Control, a control group) (see Table 5). It was indicated that the renal function was protected by the administration of a potassium citrate/sodium citrate hydrate preparation.

It was observed that the albumin concentration in urine was decreased by the administration of a potassium citrate/sodium citrate hydrate preparation as compared with that in group C (Control, control group), also in early-morning urine (see Table 4) and spot urine (see Table 5), and therefore, it was indicated that the potassium citrate/sodium citrate hydrate preparation exerted a protection effect on the renal function throughout the day.

Table 6 shows differences (mg/gCr) obtained by subtracting a value obtained by dividing each concentration of protein in spot urine before the start of administration by the urinary creatinine concentration from a value obtained by dividing each concentration of protein in spot urines after administration for 6 weeks, 12 weeks, and 24 weeks by the urinary creatinine concentration.

TABLE 6

| | | Spot Urine Protein (mg/gCr, Δ Measured value vs 0 Week) | | | |
|---|---|---|---|---|---|
| Group | N | 6 W | 12 W | 24 W$^f$ | 6-24 W$^{e,k}$ (85-90) |
| Control | 28-29 | 6.5 ±28.0$^d$ (-0.55) | 6.8 ±29.4 (0.45) | 10.9 ±24.1 (0.3) | 8.1 ±27.0$^a$ (0) |
| Citrate | 29-31 | -1.6 ±26.9 (0.5) | -3.6 ±30.8 (0.5) | -1.8 ±25.6$^{e,h,j}$ (-1.7) | -2.3 ±27.6$^{b,g,i,l}$ (0.2) |
| Bicarbonate | 27-31 | 6.9 ±19.0 (1.2) | 10.6 ±35.9 (2.7) | 17.0 ±33.6 (4.7) | 11.7 ±30.8 (2.7) |

Mean ± SD ( ): Median
$^a$p = 0.0329, $^b$p = 0.0258, $^c$p = 0.0005, and $^d$p = 0.0097 vs Bicarbonate (Mann-Whitney) $^e$p = 0.0018, $^f$p = 0.0225 (Kruskal-Wallis), and $^g$p = 0.0010, and $^h$p = 0.0185 vs Bicarbonate (Dunn) $^i$p = 0.0124 and $^j$p = 0.0565 vs Control (Student-t) $^k$p = 0.0033 (1 way ANOVA) and $^l$p = 0.0429 vs Control (Tukey)

In group A (Citrate, an administration group of a potassium citrate/sodium citrate hydrate preparation), it was observed that the protein concentration in spot urine after the administration tended to become lower as compared with that before the start of administration. Such a tendency was not observed in group B (Bicarbonate, an administration group of a sodium bicarbonate preparation) and in group C (Control, control group) (see Table 6).

Further, in group A (Citrate, an administration group of a potassium citrate/sodium citrate hydrate preparation), the value of each concentration of protein in early-morning urines after administration for 6 to 24 weeks was lower than those in group B (Bicarbonate, an administration group of a sodium bicarbonate preparation) and group C (Control, a control group), and therefore, it was indicated that the renal function was protected.

Table 7 shows osmotic pressure values (mOsm/kg H$_2$O) of early-morning urines after administration for 6 weeks, 12 weeks, and 24 weeks.

TABLE 7

| | | Urine Osmotic Pressure (mOsm/kgH$_2$O) | | | | |
|---|---|---|---|---|---|---|
| Group | N | 0 W | 6 W | 12 W | 24 W | 6-24 W (89-91) |
| Control | 30-31 | 479 ± 165 (499) | 468 ± 162 (481) | 462 ± 177 (428) | 463 ± 204 (406) | 464 ± 180 (437) |
| Citrate | 29-31 | 442 ± 166 (419) | 430 ± 156 (387) | 457 ± 188 (432) | 479 ± 178 (444) | 452 ± 173 (418) |
| Bicarbonate | 27-31 | 501 ± 234 (466) | 509 ± 215 (451) | 497 ± 206 (442) | 513 ± 239 (431) | 506 ± 218 (447) |

Mean +/− SD ( ): Median
Not Significant between Groups (Mann-Whitney)
Not Significant vs 0 week (Wilcoxon)
Not Significant between Groups (Kruskal-Wallis & Dunn)
(No significant difference among groups in week 0)

In group A (Citrate, an administration group of a potassium citrate/sodium citrate hydrate preparation), it was observed that the osmotic pressure of early-morning urine after the administration tended to become lower as compared with that before the start of administration. Further, in group B (Bicarbonate, an administration group of a sodium bicarbonate preparation), it was observed that the osmotic pressure of early-morning urine after the administration tended to be maintained as compared with that before the start of administration, but in group C (Control, control group), it was observed that the osmotic pressure of early-morning urine after the administration tended to be decreased as compared with that before the start of administration (see Table 7).

It was suggested that by the administration of a potassium citrate/sodium citrate hydrate preparation, the urinary concentrating capacity as the renal tubular function was maintained or improved.

Figure 2:
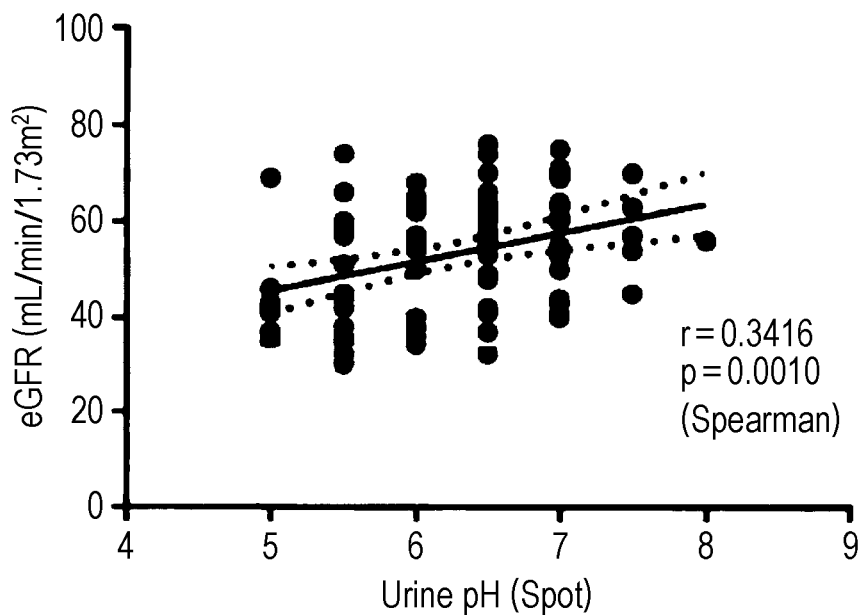
FIG. 2 is a diagram showing a correlation between the pH of spot urine and the eGFR in an administration group of a potassium citrate/sodium citrate hydrate preparation.
Figure 3:
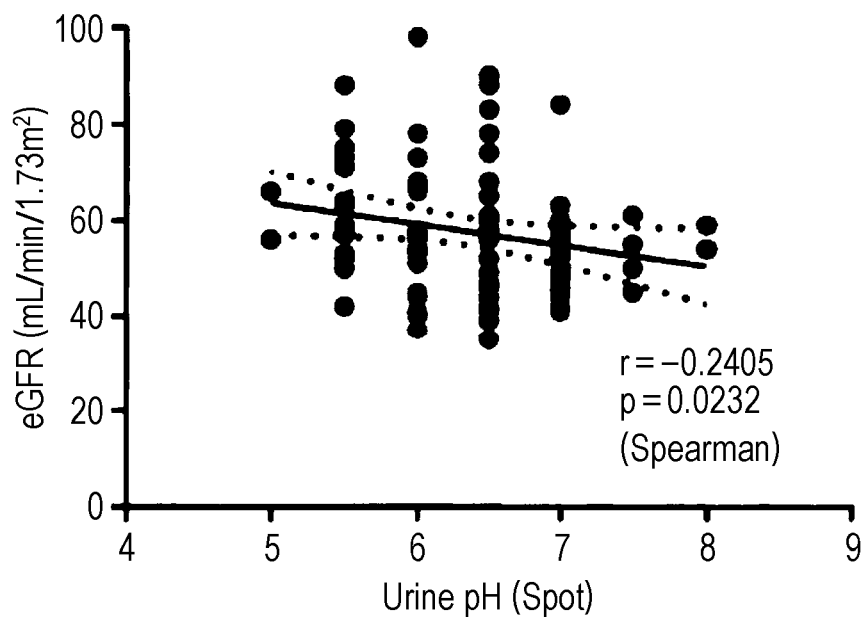
FIG. 3 is a diagram showing a correlation between the pH of spot urine and the eGFR in an administration group of a sodium bicarbonate preparation.
Figure 4:
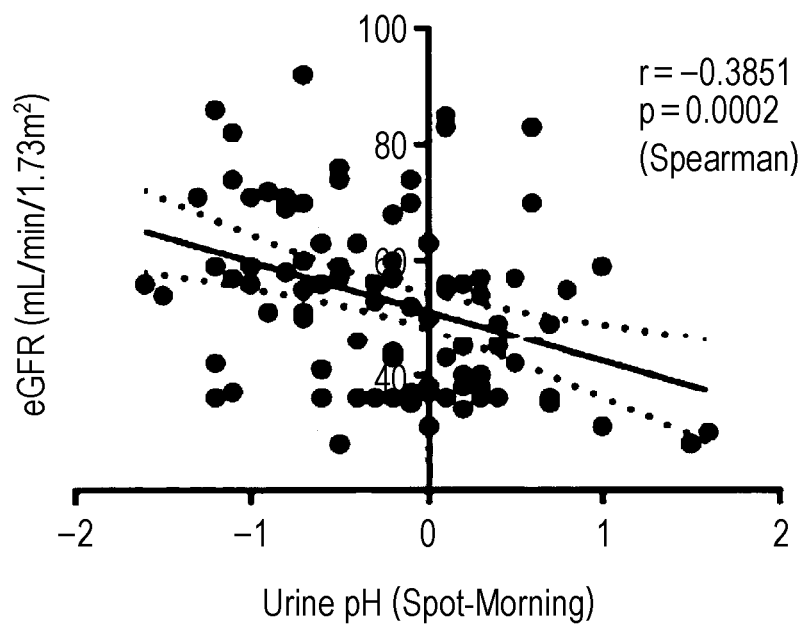
FIG. 4 is a diagram showing a correlation between the difference in pH between spot urine and early-morning urine and the eGFR in a control group.
Figure 5:
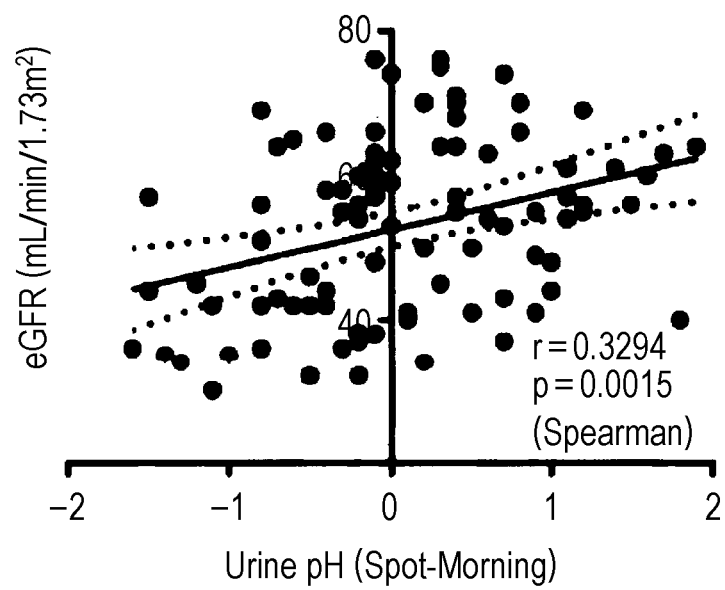
FIG. 5 is a diagram showing a correlation between the difference in pH between spot urine and early-morning urine and the eGFR in an administration group of a potassium citrate/sodium citrate hydrate preparation.
Figure 6:
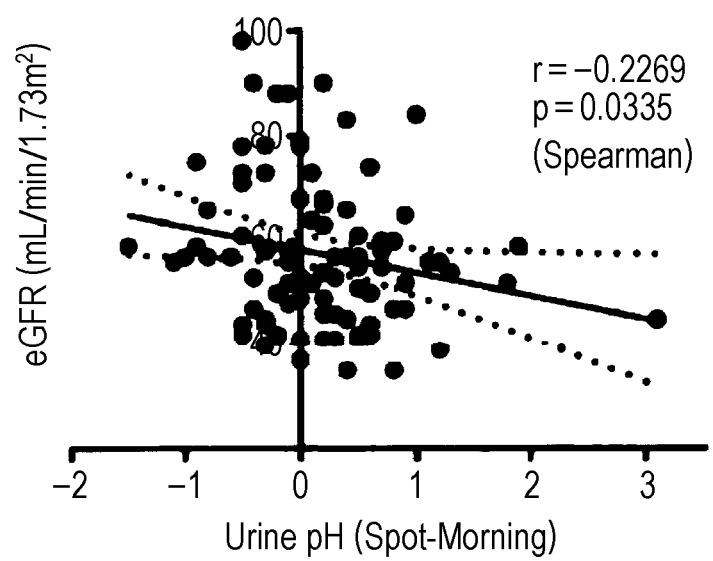
FIG. 6 is a diagram showing a correlation between the difference in pH between spot urine and early-morning urine and the eGFR in an administration group of a sodium bicarbonate preparation.

Further, for each of group A (Citrate, an administration group of a potassium citrate/sodium citrate hydrate preparation), group B (Bicarbonate, an administration group of a sodium bicarbonate preparation), and group C (Control, a control group), each pH of urines (spot urine, Spot in FIGS. 1 to 3) collected after the lapse of 2 to 5 hours from the administration in the morning was measured, and the relationship with the eGFR was plotted (FIGS. 1 to 3). In addition, each pH of urines (spot urines) collected after the lapse of 2 to 5 hours from the administration in the morning and each pH of early-morning urine were measured, and the relationship between the difference (the pH of spot urine— the pH of early-morning urine, Spot-Morning in FIGS. 4 to 6) and the eGFR was plotted (FIGS. 4 to 6). As a result, a significant correlation was observed between the value of "pH of spot urine" and the eGFR only in group A (Citrate, an administration group of a potassium citrate/sodium citrate hydrate preparation) (FIG. 2), and a significant correlation was also observed between the value of "pH of spot urine— pH of early-morning urine" and the eGFR (FIG. 5).

INDUSTRIAL APPLICABILITY

By the pharmaceutical composition provided by the present invention, the kidney is protected, and the renal tubular function is maintained or improved. Further, by the pharmaceutical composition provided by the present invention, the function of the kidney is evaluated.

The invention claimed is:
1. A method for renal protection in a mammalian subject suffering from chronic kidney disease, comprising administering to a subject in need of the renal protection an effective amount of a pharmaceutical composition comprising a mixture of sodium citrate or a hydrate thereof and potassium citrate or a hydrate thereof, wherein the renal protection is one or more selected from the group consisting of:
   (i) suppression of increase in 8-OHdG concentration in urine,
   (ii) suppression of increase in $\beta_2$-microglobulin concentration in urine,
   (iii) suppression of the increase in albumin concentration in urine,
   (iv) suppression of increase in protein concentration in urine, and
   (v) suppression of the decrease in osmotic pressure of urine; and
   wherein the mammalian subject is not suffering from metabolic acidosis.
2. The method according to claim 1, wherein the pharmaceutical composition further comprises anhydrous citric acid.
3. The method according to claim 1, wherein the mixture of sodium citrate or the hydrate thereof and potassium citrate or the hydrate thereof is administered at 1 to 3 g per day.
4. The method according to claim 1, wherein the mixture of sodium citrate or the hydrate thereof and potassium citrate or the hydrate thereof is administered at 1 to 1.5 g per day.
5. The method according to claim 1, wherein the mammalian subject suffering from chronic kidney disease is a patient with chronic kidney disease of stage G2 or more and G3b or less.
6. The method according to claim 1, wherein the pharmaceutical composition is administered for 6 weeks or more.
7. The method according to claim 1, wherein the molar ratio of potassium citrate to sodium citrate is 0.85:1.15 to 1.15:0.85.
8. The method according to claim 1, wherein the mammalian subject suffering from chronic kidney disease is a patient with chronic kidney disease of microalbuminuria or macroalbuminuria.

* * * * *